US010543102B2

(12) United States Patent
Kueenzi et al.

(10) Patent No.: US 10,543,102 B2
(45) Date of Patent: Jan. 28, 2020

(54) LOW PROFILE INTERVERTEBRAL IMPLANT

(71) Applicant: DePuy Synthes Products, Inc., Raynham, MA (US)

(72) Inventors: Thomas Kueenzi, Magden (CH); Ryan T. Walsh, Douglassville, PA (US); Thomas Pepe, West Chester, PA (US); Markus Hunziker, Aaru (CH); David Koch, North Logan, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/826,272

(22) Filed: Aug. 14, 2015

(65) Prior Publication Data
US 2015/0342750 A1 Dec. 3, 2015

Related U.S. Application Data

(63) Continuation of application No. 14/635,480, filed on Mar. 2, 2015, now Pat. No. 9,744,049, which is a (Continued)

(51) Int. Cl.
*A61F 2/44* (2006.01)
*A61B 17/70* (2006.01)
(Continued)

(52) U.S. Cl.
CPC .............. *A61F 2/4425* (2013.01); *A61F 2/44* (2013.01); *A61F 2/447* (2013.01); *A61F 2/4455* (2013.01);
(Continued)

(58) Field of Classification Search
CPC ...................................................... A61F 2/445
See application file for complete search history.

(56) References Cited

U.S. PATENT DOCUMENTS 424,836 A 4/1890 Thompson
1,105,105 A 7/1914 Sherman
(Continued)

FOREIGN PATENT DOCUMENTS

AU 2004/232317 11/2010
CA 2111598 A1 6/1994
(Continued)

OTHER PUBLICATIONS

U.S. Appl. No. 61/535,726, filed Sep. 16, 2011, Zaveloff.
(Continued)

*Primary Examiner* — Samuel S Hanna
(74) *Attorney, Agent, or Firm* — BakerHostetler

(57) ABSTRACT

The present invention is directed to a low profile intervertebral implant for implantation in an intervertebral disc space in-between adjacent vertebral bodies. The intervertebral implant includes a plate preferably coupled to a spacer. The plate is preferably formed from a first material and the spacer is preferably formed from a second material, the first material being different from the second material. The plate is preferably sized and configured so that the plate does not extend beyond the perimeter of the spacer. In this manner, the plate preferably does not increase the height profile of the spacer and the plate may be implanted within the intervertebral disc space in conjunction with the spacer.

21 Claims, 10 Drawing Sheets

Related U.S. Application Data continuation of application No. 13/594,965, filed on Aug. 27, 2012, now Pat. No. 9,005,295, which is a continuation of application No. 12/743,098, filed as application No. PCT/US2008/082473 on Nov. 5, 2008, now Pat. No. 8,540,774.

(60) Provisional application No. 60/988,661, filed on Nov. 16, 2007.

(51) Int. Cl.
<br>　　A61B 17/80　　(2006.01)
<br>　　A61B 17/86　　(2006.01)
<br>　　A61F 2/28　　(2006.01)
<br>　　A61F 2/30　　(2006.01)

(52) U.S. Cl.
<br>　　CPC ....... *A61B 17/7059* (2013.01); *A61B 17/8033* (2013.01); *A61B 17/86* (2013.01); *A61F 2/28* (2013.01); *A61F 2002/302* (2013.01); *A61F 2002/305* (2013.01); *A61F 2002/30077* (2013.01); *A61F 2002/30092* (2013.01); *A61F 2002/30331* (2013.01); *A61F 2002/30387* (2013.01); *A61F 2002/30485* (2013.01); *A61F 2002/30507* (2013.01); *A61F 2002/30578* (2013.01); *A61F 2002/30604* (2013.01); *A61F 2002/30787* (2013.01); *A61F 2210/0014* (2013.01); *A61F 2210/0066* (2013.01); *A61F 2220/0025* (2013.01); *A61F 2220/0033* (2013.01); *A61F 2230/0065* (2013.01); *A61F 2230/0073* (2013.01); *A61F 2310/00023* (2013.01); *A61F 2310/00323* (2013.01); *A61F 2310/00359* (2013.01)

(56) References Cited

U.S. PATENT DOCUMENTS

| | | |
|---|---|---|
| 1,200,797 A | 10/1916 | Barbe |
| 2,151,919 A | 3/1939 | Jacobson |
| 2,372,888 A | 4/1945 | Edward |
| 2,621,145 A | 12/1952 | Sano |
| 2,782,827 A | 2/1957 | Joseph |
| 2,906,311 A | 9/1959 | Boyd |
| 2,972,367 A | 2/1961 | Wootton |
| 3,062,253 A | 11/1962 | Melvin |
| 3,272,249 A | 9/1966 | Houston |
| 3,350,103 A | 10/1967 | Ahlstone |
| 3,426,364 A | 2/1969 | Lumb |
| 3,561,075 A | 2/1971 | Selinko |
| 3,579,831 A | 5/1971 | Stevens et al. |
| 3,707,303 A | 12/1972 | Petri |
| 3,810,703 A | 5/1974 | Pasbrig |
| 3,867,728 A | 2/1975 | Stubstad et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,298,993 A | 11/1981 | Potekhin |
| 4,299,902 A | 11/1981 | Soma et al. |
| 4,349,921 A | 9/1982 | Kuntz |
| 4,388,921 A | 6/1983 | Sutter et al. |
| 4,394,370 A | 7/1983 | Jefferies |
| 4,450,591 A | 5/1984 | Rappaport |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Caspar et al. |
| 4,512,038 A | 4/1985 | Alexander et al. |
| 4,545,374 A | 10/1985 | Jacobson |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,714,469 A | 12/1987 | Kenna |
| 4,717,115 A | 1/1988 | Schmitz |
| 4,743,256 A | 5/1988 | Brantigan |
| 4,781,721 A | 11/1988 | Grundei |
| 4,793,335 A | 12/1988 | Frey et al. |
| 4,804,290 A | 2/1989 | Balsells |
| 4,812,094 A | 3/1989 | Grube |
| 4,829,152 A | 5/1989 | Rostoker |
| 4,834,757 A | 5/1989 | Brantigan |
| 4,858,603 A | 8/1989 | Clemow et al. |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,932,973 A | 6/1990 | Gendler |
| 4,936,851 A | 6/1990 | Fox et al. |
| 4,946,378 A | 8/1990 | Hirayama et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney |
| 4,978,350 A | 12/1990 | Wagenknecht |
| 4,994,084 A | 2/1991 | Brennan |
| 4,997,432 A | 3/1991 | Keller |
| 5,006,120 A | 4/1991 | Carter |
| 5,010,783 A | 4/1991 | Sparks et al. |
| 5,017,069 A | 5/1991 | Stencel |
| 5,020,949 A | 6/1991 | Davidson et al. |
| 5,026,373 A | 6/1991 | Ray et al. |
| 5,030,220 A | 7/1991 | Howland |
| 5,047,058 A | 9/1991 | Roberts et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Tormala et al. |
| 5,085,660 A | 2/1992 | Lin |
| 5,096,150 A | 3/1992 | Westwood |
| 5,108,438 A | 4/1992 | Stone et al. |
| 5,112,354 A | 5/1992 | Sires |
| 5,116,374 A | 5/1992 | Stone |
| 5,118,235 A | 6/1992 | Dill |
| 5,139,424 A | 8/1992 | Yli-Urpo |
| 5,147,404 A | 9/1992 | Downey |
| 5,163,949 A | 11/1992 | Bonutti |
| 5,163,960 A | 11/1992 | Bonutti |
| 5,180,381 A | 1/1993 | Aust et al. |
| 5,192,327 A | 3/1993 | Brantigan |
| 5,197,971 A | 3/1993 | Bonutti |
| 5,201,736 A | 4/1993 | Strauss |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stencel |
| 5,258,031 A | 11/1993 | Salib et al. |
| 5,269,785 A | 12/1993 | Bonutti |
| 5,275,601 A | 1/1994 | Gogolewski et al. |
| 5,281,226 A | 1/1994 | Davydov et al. |
| 5,282,861 A | 2/1994 | Kaplan |
| 5,284,655 A | 2/1994 | Bogdansky et al. |
| 5,290,312 A | 3/1994 | Kojimoto et al. |
| 5,295,994 A | 3/1994 | Bonutti |
| 5,298,254 A | 3/1994 | Prewett et al. |
| 5,304,021 A | 4/1994 | Oliver et al. |
| 5,306,307 A | 4/1994 | Senter et al. |
| 5,306,308 A | 4/1994 | Fuhrmann |
| 5,306,309 A | 4/1994 | Wagner et al. |
| 5,314,476 A | 5/1994 | Prewett et al. |

(56) References Cited

U.S. PATENT DOCUMENTS

| | | |
|---|---|---|
| 5,314,477 A | 5/1994 | Marnay |
| 5,329,846 A | 7/1994 | Bonutti |
| 5,330,535 A | 7/1994 | Moser et al. |
| 5,331,975 A | 7/1994 | Bonutti |
| 5,345,927 A | 9/1994 | Bonutti |
| 5,348,788 A | 9/1994 | White |
| 5,368,593 A | 11/1994 | Stark |
| 5,380,323 A | 1/1995 | Howland |
| 5,385,583 A | 1/1995 | Cotrel |
| 5,397,364 A | 3/1995 | Kozak et al. |
| 5,403,317 A | 4/1995 | Bonutti |
| 5,403,348 A | 4/1995 | Bonutti |
| 5,405,391 A | 4/1995 | Hednerson et al. |
| 5,411,348 A | 5/1995 | Balsells |
| 5,423,817 A | 6/1995 | Lin |
| 5,425,772 A | 6/1995 | Brantigan |
| 5,431,658 A | 7/1995 | Moskovich |
| 5,439,684 A | 8/1995 | Prewett et al. |
| 5,441,538 A | 8/1995 | Bonutti |
| 5,443,514 A | 8/1995 | Steffee |
| 5,443,515 A | 8/1995 | Cohen et al. |
| 5,454,365 A | 10/1995 | Bonutti |
| 5,458,638 A | 10/1995 | Kuslich et al. |
| 5,458,641 A | 10/1995 | Ramirez |
| 5,458,643 A | 10/1995 | Oka et al. |
| 5,464,426 A | 11/1995 | Bonutti |
| 5,478,342 A | 12/1995 | Kohrs |
| 5,484,437 A | 1/1996 | Michelson |
| 5,487,744 A | 1/1996 | Howland |
| 5,489,308 A | 2/1996 | Kuslich et al. |
| 5,496,348 A | 3/1996 | Bonutti |
| 5,507,818 A | 4/1996 | McLaughlin |
| 5,514,153 A | 5/1996 | Bonutti |
| 5,514,180 A | 5/1996 | Heggeness et al. |
| 5,520,690 A | 5/1996 | Errico et al. |
| 5,522,846 A | 6/1996 | Bonutti |
| 5,522,899 A | 6/1996 | Michelson |
| 5,527,343 A | 6/1996 | Bonutti |
| 5,531,746 A | 7/1996 | Errico et al. |
| 5,534,012 A | 7/1996 | Bonutti |
| 5,534,030 A | 7/1996 | Navarro et al. |
| 5,534,031 A | 7/1996 | Matsuzaki et al. |
| 5,534,032 A | 7/1996 | Hodorek |
| 5,545,222 A | 8/1996 | Bonutti |
| 5,545,842 A | 8/1996 | Balsells |
| 5,549,612 A | 8/1996 | Yapp et al. |
| 5,549,630 A | 8/1996 | Bonutti |
| 5,549,631 A | 8/1996 | Bonutti |
| 5,549,679 A | 8/1996 | Kuslich |
| 5,550,172 A | 8/1996 | Regula et al. |
| 5,554,191 A | 9/1996 | Lahille et al. |
| 5,556,430 A | 9/1996 | Gendler |
| 5,556,431 A | 9/1996 | Buttner-Janz |
| 5,569,305 A | 10/1996 | Bonutti |
| 5,569,308 A | 10/1996 | Sottosanti |
| 5,570,983 A | 11/1996 | Hollander |
| 5,571,109 A * | 11/1996 | Bertagnoli ........... A61B 17/025 606/86 A |
| 5,571,190 A | 11/1996 | Ulrich et al. |
| 5,571,192 A | 11/1996 | Schonhoffer |
| 5,577,517 A | 11/1996 | Bonutti |
| 5,578,034 A | 11/1996 | Estes |
| 5,584,862 A | 12/1996 | Bonutti |
| 5,593,409 A | 1/1997 | Michelson |
| 5,593,425 A | 1/1997 | Bonutti |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,620,448 A | 4/1997 | Puddu |
| 5,624,462 A | 4/1997 | Bonutti |
| 5,642,960 A | 7/1997 | Salice |
| 5,645,596 A | 7/1997 | Kim et al. |
| 5,645,606 A | 7/1997 | Oehy et al. |
| 5,653,708 A | 8/1997 | Howland |
| 5,662,710 A | 9/1997 | Bonutti |
| 5,667,520 A | 9/1997 | Bonutti |
| 5,669,909 A | 9/1997 | Zdeblick et al. |
| 5,674,296 A | 10/1997 | Bryan et al. |
| 5,676,666 A | 10/1997 | Oxland |
| 5,676,699 A | 10/1997 | Gogolewski |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,685,826 A | 11/1997 | Bonutti |
| 5,694,951 A | 12/1997 | Bonutti |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,707,390 A | 1/1998 | Bonutti |
| 5,713,899 A * | 2/1998 | Marnay ................ A61F 2/4455 623/17.11 |
| 5,713,900 A | 2/1998 | Benzel et al. |
| 5,716,325 A | 2/1998 | Bonutti |
| 5,725,531 A | 3/1998 | Shapiro |
| 5,725,588 A | 3/1998 | Errico et al. |
| 5,728,159 A | 3/1998 | Stroever et al. |
| 5,733,306 A | 3/1998 | Bonutti |
| 5,735,853 A | 4/1998 | Olerud |
| 5,735,875 A | 4/1998 | Bonutti |
| 5,735,905 A | 4/1998 | Parr |
| 5,755,796 A | 5/1998 | Ibo et al. |
| 5,755,798 A | 5/1998 | Papavero et al. |
| 5,766,251 A | 6/1998 | Koshino |
| 5,766,252 A | 6/1998 | Henry et al. |
| 5,766,253 A | 6/1998 | Brosnahan, III |
| 5,772,661 A | 6/1998 | Michelson |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,782,919 A | 7/1998 | Zdeblick et al. |
| 5,785,710 A | 7/1998 | Michelson |
| 5,800,433 A | 9/1998 | Benzel et al. |
| 5,827,318 A | 10/1998 | Bonutti |
| 5,836,948 A | 11/1998 | Zuchermann et al. |
| 5,845,645 A | 12/1998 | Bonutti |
| 5,860,973 A | 1/1999 | Michelson |
| 5,860,997 A | 1/1999 | Bonutti |
| 5,861,041 A | 1/1999 | Tienboon |
| 5,865,845 A | 2/1999 | Thalgott |
| 5,865,849 A | 2/1999 | Stone |
| 5,872,915 A | 2/1999 | Dykes et al. |
| 5,876,402 A | 3/1999 | Errico et al. |
| 5,876,452 A | 3/1999 | Athansiou et al. |
| 5,879,389 A | 3/1999 | Koshino |
| 5,885,299 A | 3/1999 | Winslow et al. |
| 5,888,196 A | 3/1999 | Bonutti |
| 5,888,219 A | 3/1999 | Bonutti |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,906,616 A | 5/1999 | Pavlov et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |

(56) References Cited

U.S. PATENT DOCUMENTS

| | | |
|---|---|---|
| 5,928,267 A | 7/1999 | Bonutti |
| 5,931,838 A | 8/1999 | Vito |
| 5,935,131 A | 8/1999 | Bonutti |
| 5,941,900 A | 8/1999 | Bonutti |
| 5,944,755 A | 8/1999 | Stone |
| 5,951,558 A | 9/1999 | Fiz |
| 5,954,722 A | 9/1999 | Bono |
| 5,954,739 A | 9/1999 | Bonutti |
| 5,958,314 A | 9/1999 | Draenet |
| 5,964,807 A | 10/1999 | Gan et al. |
| 5,968,098 A | 10/1999 | Winslow |
| 5,972,031 A | 10/1999 | Biedermann |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,001,099 A | 12/1999 | Huebner |
| 6,008,433 A | 12/1999 | Stone |
| 6,010,525 A | 1/2000 | Bonutti |
| 6,013,853 A | 1/2000 | Athanasiou et al. |
| 6,017,305 A | 1/2000 | Bonutti |
| 6,017,345 A | 1/2000 | Richelsoph |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,042,596 A | 3/2000 | Bonutti |
| 6,045,579 A | 4/2000 | Hochshuler et al. |
| 6,045,580 A | 4/2000 | Scarborough et al. |
| 6,056,749 A | 5/2000 | Kuslich |
| 6,059,817 A | 5/2000 | Bonutti |
| 6,066,175 A | 5/2000 | Henderson et al. |
| 6,077,292 A | 6/2000 | Bonutti |
| 6,080,158 A | 6/2000 | Lin |
| 6,080,193 A | 6/2000 | Hochshuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,102,928 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,132,472 A | 10/2000 | Bonutti |
| 6,136,001 A | 10/2000 | Michelson |
| 6,139,550 A | 10/2000 | Michelson |
| RE36,974 E | 11/2000 | Bonutti |
| 6,143,030 A | 11/2000 | Schroder |
| 6,143,033 A | 11/2000 | Paul et al. |
| 6,146,421 A | 11/2000 | Gordon |
| 6,156,070 A | 12/2000 | Incavo et al. |
| 6,159,215 A | 12/2000 | Urbahns |
| 6,159,234 A | 12/2000 | Bonutti |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,203,565 B1 | 3/2001 | Bonutti et al. |
| 6,206,922 B1 | 3/2001 | Zdeblick et al. |
| 6,217,617 B1 | 4/2001 | Bonutti |
| 6,224,602 B1 | 5/2001 | Hayes |
| 6,231,592 B1 | 5/2001 | Bonutti et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,277,136 B1 | 8/2001 | Bonutti |
| 6,287,325 B1 | 9/2001 | Bonutti |
| 6,306,139 B1 | 10/2001 | Fuentes |
| 6,322,562 B1 | 11/2001 | Wolter |
| 6,331,179 B1 | 12/2001 | Freid et al. |
| 6,342,074 B1 | 1/2002 | Simpson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti |
| 6,371,986 B1 | 4/2002 | Bagby |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,398,811 B1 | 6/2002 | McKay |
| 6,413,259 B1 | 7/2002 | Lyons et al. |
| 6,423,063 B1 | 7/2002 | Bonutti |
| 6,432,106 B1 | 8/2002 | Fraser |
| 6,443,987 B1 | 9/2002 | Bryan |
| 6,447,512 B1 | 9/2002 | Landry et al. |
| 6,447,516 B1 | 9/2002 | Bonutti |
| 6,447,546 B1 | 9/2002 | Bramlet et al. |
| 6,451,042 B1 | 9/2002 | Bonutti |
| 6,454,771 B1 | 9/2002 | Michelson |
| 6,458,158 B1 | 10/2002 | Anderson et al. |
| 6,461,359 B1 | 10/2002 | Tribus et al. |
| 6,464,713 B2 | 10/2002 | Bonutti |
| 6,468,289 B1 | 10/2002 | Bonutti |
| 6,468,293 B2 | 10/2002 | Bonutti et al. |
| 6,468,311 B2 | 10/2002 | Boyd et al. |
| 6,471,724 B2 | 10/2002 | Zdeblick et al. |
| 6,475,230 B1 | 11/2002 | Bonutti |
| 6,482,233 B1 | 11/2002 | Aebi et al. |
| 6,500,195 B2 | 12/2002 | Bonutti |
| 6,503,250 B2 | 1/2003 | Paul |
| 6,503,267 B2 | 1/2003 | Bonutti et al. |
| 6,503,277 B2 | 1/2003 | Bonutti |
| 6,511,509 B1 | 1/2003 | Ford et al. |
| 6,524,312 B2 | 2/2003 | Landry et al. |
| 6,543,455 B2 | 4/2003 | Bonutti |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,565,605 B2 | 5/2003 | Goble et al. |
| 6,569,187 B1 | 5/2003 | Bonutti |
| 6,569,201 B2 | 5/2003 | Moumene et al. |
| 6,575,975 B2 | 6/2003 | Brace et al. |
| 6,575,982 B1 | 6/2003 | Bonutti |
| 6,576,017 B2 | 6/2003 | Foley et al. |
| 6,579,290 B1 | 6/2003 | Hardcastle et al. |
| 6,585,750 B2 | 7/2003 | Bonutti et al. |
| 6,592,531 B2 | 7/2003 | Bonutti |
| 6,592,609 B1 | 7/2003 | Bonutti |
| 6,592,624 B1 | 7/2003 | Fraser et al. |
| 6,602,291 B1 | 8/2003 | Ray et al. |
| 6,605,090 B1 | 8/2003 | Trieu et al. |
| 6,607,534 B2 | 8/2003 | Bonutti |
| 6,616,671 B2 | 9/2003 | Landry et al. |
| 6,620,163 B1 | 9/2003 | Michelson |
| 6,620,181 B1 | 9/2003 | Bonutti |
| 6,623,486 B1 | 9/2003 | Weaver et al. |
| 6,629,998 B1 | 10/2003 | Lin |
| 6,630,000 B1 | 10/2003 | Bonutti |

(56) References Cited

U.S. PATENT DOCUMENTS

| | | |
|---|---|---|
| 6,635,073 B2 | 10/2003 | Bonutti |
| 6,638,309 B2 | 10/2003 | Bonutti |
| 6,638,310 B2 | 10/2003 | Lin et al. |
| 6,645,212 B2 | 11/2003 | Goldhahn et al. |
| 6,652,525 B1 | 11/2003 | Assaker et al. |
| 6,652,532 B2 | 11/2003 | Bonutti |
| 6,656,181 B2 | 12/2003 | Dixon et al. |
| 6,679,887 B2 | 1/2004 | Nicholson et al. |
| 6,682,561 B2 | 1/2004 | Songer et al. |
| 6,682,563 B2 | 1/2004 | Scharf |
| 6,695,846 B2 | 2/2004 | Richelsoph et al. |
| 6,695,851 B2 | 2/2004 | Zbeblick et al. |
| 6,702,821 B2 | 3/2004 | Bonutti |
| 6,702,856 B2 | 3/2004 | Bonutti |
| 6,706,067 B2 | 3/2004 | Shimp et al. |
| 6,709,456 B2 | 3/2004 | Langberg et al. |
| 6,712,818 B1 | 3/2004 | Michelson |
| 6,719,803 B2 | 4/2004 | Bonutti |
| 6,730,127 B2 | 5/2004 | Michelson |
| 6,736,850 B2 | 5/2004 | Davis |
| 6,736,853 B2 | 5/2004 | Bonutti |
| 6,743,257 B2 | 6/2004 | Castro |
| 6,761,738 B1 | 7/2004 | Boyd |
| 6,761,739 B2 | 7/2004 | Shepard |
| 6,770,078 B2 | 8/2004 | Bonutti |
| 6,770,096 B2 | 8/2004 | Bolger et al. |
| 6,776,938 B2 | 8/2004 | Bonutti |
| 6,786,909 B1 | 9/2004 | Dransfeld |
| 6,800,092 B1 | 10/2004 | Williams et al. |
| 6,800,093 B2 | 10/2004 | Nicholson et al. |
| 6,805,714 B2 | 10/2004 | Sutcliffe |
| 6,808,537 B2 | 10/2004 | Michelson |
| 6,824,564 B2 | 11/2004 | Crozet |
| 6,833,006 B2 | 12/2004 | Foley et al. |
| 6,835,198 B2 | 12/2004 | Bonutti |
| 6,837,905 B1 | 1/2005 | Lieberman |
| 6,849,093 B2 | 2/2005 | Michlson |
| 6,855,167 B2 | 2/2005 | Shimp et al. |
| 6,855,168 B2 | 2/2005 | Crozet |
| 6,860,885 B2 | 3/2005 | Bonutti |
| 6,860,904 B2 | 3/2005 | Bonutti |
| 6,863,673 B2 | 3/2005 | Gerbec et al. |
| 6,872,915 B2 | 3/2005 | Koga et al. |
| 6,884,242 B2 | 4/2005 | LeHuec et al. |
| 6,890,334 B2 | 5/2005 | Brace et al. |
| 6,896,701 B2 | 5/2005 | Boyd et al. |
| 6,899,735 B2 | 5/2005 | Coates et al. |
| 6,902,578 B1 | 6/2005 | Anderson et al. |
| 6,905,517 B2 | 6/2005 | Bonutti |
| 6,908,466 B1 | 6/2005 | Bonutti et al. |
| 6,916,320 B2 | 7/2005 | Michelson |
| 6,923,756 B2 | 8/2005 | Sudakov et al. |
| 6,932,835 B2 | 8/2005 | Bonutti et al. |
| 6,953,477 B2 | 10/2005 | Berry |
| 6,962,606 B2 | 11/2005 | Michelson |
| 6,964,664 B2 | 11/2005 | Freid et al. |
| 6,964,687 B1 | 11/2005 | Bernard et al. |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 6,989,029 B2 | 1/2006 | Bonutti |
| 6,990,982 B1 | 1/2006 | Bonutti |
| 7,001,385 B2 | 2/2006 | Bonutti |
| 7,001,432 B2 | 2/2006 | Keller et al. |
| 7,018,412 B2 | 3/2006 | Ferreira et al. |
| 7,018,416 B2 | 3/2006 | Hanson et al. |
| 7,033,394 B2 | 4/2006 | Michelson |
| 7,041,135 B2 | 5/2006 | Michelson |
| 7,044,968 B1 | 5/2006 | Yaccarino et al. |
| 7,044,972 B2 | 5/2006 | Mathys et al. |
| 7,048,755 B2 | 5/2006 | Bonutti et al. |
| 7,048,765 B1 | 5/2006 | Grooms et al. |
| 7,060,097 B2 | 6/2006 | Fraser et al. |
| 7,066,961 B2 | 6/2006 | Michelson |
| 7,070,557 B2 | 7/2006 | Bonutti |
| 7,077,864 B2 | 7/2006 | Byrd, III et al. |
| 7,087,073 B2 | 8/2006 | Bonutti |
| 7,094,251 B2 | 8/2006 | Bonutti et al. |
| 7,104,996 B2 | 9/2006 | Bonutti |
| 7,112,222 B2 | 9/2006 | Fraser et al. |
| 7,112,223 B2 | 9/2006 | Davis |
| 7,114,500 B2 | 10/2006 | Bonutti |
| 7,128,753 B1 | 10/2006 | Bonutti et al. |
| 7,134,437 B2 | 11/2006 | Bonutti |
| 7,135,024 B2 | 11/2006 | Cook et al. |
| 7,135,043 B2 | 11/2006 | Nakahara et al. |
| 7,137,984 B2 | 11/2006 | Michelson |
| 7,147,652 B2 | 12/2006 | Bonutti et al. |
| 7,147,665 B1 | 12/2006 | Bryan et al. |
| 7,163,561 B2 | 1/2007 | Michelson |
| 7,172,627 B2 | 2/2007 | Fiere et al. |
| 7,172,672 B2 | 2/2007 | Silverbrook |
| 7,208,013 B1 | 4/2007 | Bonutti |
| 7,217,273 B2 | 5/2007 | Bonutti |
| 7,217,290 B2 | 5/2007 | Bonutti |
| 7,226,452 B2 | 6/2007 | Zubok |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,255,698 B2 | 8/2007 | Michelson |
| 7,276,082 B2 | 10/2007 | Zdeblick et al. |
| 7,311,719 B2 | 12/2007 | Bonutti |
| 7,320,708 B1 | 1/2008 | Bernstein |
| 7,323,011 B2 | 1/2008 | Shepard et al. |
| 7,329,263 B2 | 2/2008 | Bonutti et al. |
| 7,398,623 B2 | 7/2008 | Martel et al. |
| 7,429,266 B2 | 9/2008 | Bonutti et al. |
| 7,442,209 B2 | 10/2008 | Michelson |
| 7,462,200 B2 | 12/2008 | Bonutti |
| 7,481,831 B2 | 1/2009 | Bonutti |
| 7,485,145 B2 | 2/2009 | Purcell |
| 7,491,237 B2 | 2/2009 | Randall et al. |
| 7,510,557 B1 | 3/2009 | Bonutti |
| 7,534,265 B1 | 5/2009 | Boyd et al. |
| 7,594,932 B2 | 9/2009 | Aferzon et al. |
| 7,601,173 B2 | 10/2009 | Messerli et al. |
| 7,608,107 B2 | 10/2009 | Michelson |
| 7,615,054 B1 | 11/2009 | Bonutti |
| 7,618,456 B2 | 11/2009 | Mathieu et al. |
| 7,621,960 B2 | 11/2009 | Boyd et al. |
| 7,625,380 B2 | 12/2009 | Drewry et al. |
| 7,635,390 B1 | 12/2009 | Bonutti |
| 7,637,951 B2 | 12/2009 | Michelson |
| 7,655,042 B2 | 2/2010 | Foley et al. |
| 7,704,279 B2 | 4/2010 | Moskowitz et al. |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,776,067 B2 | 8/2010 | Jackson |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,833,271 B2 | 11/2010 | Mitchell et al. |
| 7,837,736 B2 | 11/2010 | Bonutti |
| 7,846,188 B2 | 12/2010 | Moskowitz et al. |
| 7,846,207 B2 | 12/2010 | Lechmann et al. |
| 7,854,750 B2 | 12/2010 | Bonutti et al. |
| 7,862,616 B2 | 1/2011 | Lechmann et al. |
| 7,875,076 B2 | 1/2011 | Mathieu et al. |
| 7,879,072 B2 | 2/2011 | Bonutti et al. |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,942,903 B2 | 5/2011 | Moskowitz et al. |
| 7,959,635 B1 | 6/2011 | Bonutti |
| 7,985,255 B2 | 7/2011 | Bray et al. |
| 7,993,403 B2 | 8/2011 | Foley et al. |
| 8,062,303 B2 | 11/2011 | Berry et al. |
| 8,100,976 B2 | 1/2012 | Bray et al. |

(56) References Cited

U.S. PATENT DOCUMENTS

| | | |
|---|---|---|
| 8,105,383 B2 | 1/2012 | Michelson |
| 8,128,669 B2 | 3/2012 | Bonutti |
| 8,128,700 B2 | 3/2012 | Delurio et al. |
| 8,133,229 B1 | 3/2012 | Bonutti |
| 8,162,977 B2 | 4/2012 | Bonutti et al. |
| 8,182,532 B2 | 5/2012 | Anderson et al. |
| 8,187,329 B2 | 5/2012 | Theofilos |
| 8,211,148 B2 | 7/2012 | Zhang et al. |
| 8,273,127 B2 | 9/2012 | Jones et al. |
| 8,308,804 B2 | 11/2012 | Kureger |
| 8,328,872 B2 | 12/2012 | Duffield et al. |
| 8,343,220 B2 | 1/2013 | Michelson |
| 8,343,222 B2 | 1/2013 | Cope |
| 8,353,913 B2 | 1/2013 | Moskowitz et al. |
| 8,382,768 B2 | 2/2013 | Berry et al. |
| 8,425,522 B2 | 4/2013 | Bonutti |
| 8,425,607 B2 | 4/2013 | Waugh et al. |
| 8,444,696 B2 | 5/2013 | Michelson |
| 8,465,546 B2 | 6/2013 | Jodaitis et al. |
| 8,486,066 B2 | 7/2013 | Bonutti |
| 8,540,774 B2 | 9/2013 | Kueenzi et al. |
| 8,545,567 B1 | 10/2013 | Kreuger |
| 8,613,772 B2 | 12/2013 | Bray et al. |
| 8,623,030 B2 | 1/2014 | Bonutti |
| 8,632,552 B2 | 1/2014 | Bonutti |
| 8,641,726 B2 | 2/2014 | Bonutti |
| 8,641,743 B2 | 2/2014 | Michelson |
| 8,641,768 B2 | 2/2014 | Duffield et al. |
| 8,690,944 B2 | 4/2014 | Bonutti |
| 8,739,797 B2 | 6/2014 | Bonutti |
| 8,747,439 B2 | 6/2014 | Bonutti et al. |
| 8,764,831 B2 | 7/2014 | Lechmann et al. |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,956,417 B2 | 2/2015 | Bonutti |
| 9,005,295 B2 | 4/2015 | Kueenzi et al. |
| 9,044,322 B2 | 6/2015 | Bonutti |
| 9,044,341 B2 | 6/2015 | Bonutti |
| 9,050,152 B2 | 6/2015 | Bonutti |
| 9,149,365 B2 | 10/2015 | Lawson et al. |
| 9,241,809 B2 | 1/2016 | McDonough et al. |
| 9,364,340 B2 | 6/2016 | Lawson et al. |
| 9,414,935 B2 | 8/2016 | McDonough et al. |
| 9,463,097 B2 | 10/2016 | Lechmann et al. |
| 9,744,049 B2 | 8/2017 | Kueenzi et al. |
| 9,883,950 B2 | 2/2018 | Bertagnoli et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyee et al. |
| 2001/0023371 A1 | 9/2001 | Bonutti |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2001/0049560 A1 | 12/2001 | Paul et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029055 A1 | 3/2002 | Bonutti |
| 2002/0029084 A1 | 3/2002 | Paul et al. |
| 2002/0040246 A1 | 4/2002 | Bonutti |
| 2002/0049497 A1 | 4/2002 | Mason |
| 2002/0065517 A1 | 5/2002 | Paul |
| 2002/0082597 A1 | 6/2002 | Fraser |
| 2002/0082603 A1 | 6/2002 | Dixon et al. |
| 2002/0082803 A1 | 6/2002 | Schiffbauer |
| 2002/0091447 A1 | 7/2002 | Shimp et al. |
| 2002/0095155 A1 | 7/2002 | Michelson |
| 2002/0095160 A1 | 7/2002 | Bonutti |
| 2002/0099376 A1 | 7/2002 | Michelson |
| 2002/0099378 A1 | 7/2002 | Michelson |
| 2002/0099444 A1 | 7/2002 | Boyd et al. |
| 2002/0106393 A1 | 8/2002 | Bianchi et al. |
| 2002/0107571 A1 | 8/2002 | Foley |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | LeHuec et al. |
| 2002/0169508 A1 | 11/2002 | Songer et al. |
| 2002/0161444 A1 | 12/2002 | Choi |
| 2002/0193880 A1 | 12/2002 | Fraser |
| 2003/0004576 A1* | 1/2003 | Thalgott ............... A61F 2/4455 623/17.16 |
| 2003/0009147 A1 | 1/2003 | Bonutti |
| 2003/0023260 A1 | 1/2003 | Bonutti |
| 2003/0045939 A1 | 3/2003 | Casutt |
| 2003/0078666 A1 | 4/2003 | Michelson |
| 2003/0078668 A1 | 4/2003 | Michelson |
| 2003/0125739 A1* | 7/2003 | Bagga ................... A61F 2/4455 606/247 |
| 2003/0135277 A1 | 7/2003 | Bryan et al. |
| 2003/0153975 A1* | 8/2003 | Byrd, III ................. A61F 2/447 623/17.11 |
| 2003/0167092 A1 | 9/2003 | Foley |
| 2003/0181981 A1 | 9/2003 | Lemaire |
| 2003/0195626 A1 | 10/2003 | Huppert |
| 2003/0195632 A1 | 10/2003 | Foley et al. |
| 2003/0199881 A1 | 10/2003 | Bonutti |
| 2003/0199983 A1 | 10/2003 | Michelson |
| 2004/0010287 A1 | 1/2004 | Bonutti |
| 2004/0078078 A1 | 4/2004 | Shepard |
| 2004/0078081 A1 | 4/2004 | Ferree |
| 2004/0092929 A1 | 5/2004 | Zindrick |
| 2004/0093084 A1 | 5/2004 | Michelson |
| 2004/0097794 A1 | 5/2004 | Bonutti |
| 2004/0098016 A1 | 5/2004 | Bonutti |
| 2004/0102848 A1 | 5/2004 | Michelson |
| 2004/0102850 A1 | 5/2004 | Shepard |
| 2004/0126407 A1 | 7/2004 | Falahee |
| 2004/0133278 A1 | 7/2004 | Marino et al. |
| 2004/0138689 A1 | 7/2004 | Bonutti |
| 2004/0138690 A1 | 7/2004 | Bonutti |
| 2004/0143270 A1 | 7/2004 | Zucherman et al. |
| 2004/0143285 A1 | 7/2004 | Bonutti |
| 2004/0172033 A1 | 9/2004 | Bonutti |
| 2004/0176853 A1 | 9/2004 | Sennett et al. |
| 2004/0193181 A1 | 9/2004 | Bonutti |
| 2004/0193269 A1 | 9/2004 | Fraser et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0220668 A1 | 11/2004 | Eisermann et al. |
| 2004/0230223 A1 | 11/2004 | Bonutti et al. |
| 2004/0249377 A1 | 12/2004 | Kaes et al. |
| 2004/0254644 A1 | 12/2004 | Taylor |
| 2004/0260427 A1 | 12/2004 | Wimsatt |
| 2005/0015149 A1 | 1/2005 | Michelson |
| 2005/0021042 A1 | 1/2005 | Marnay et al. |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0113918 A1 | 5/2005 | Messerli et al. |
| 2005/0113920 A1* | 5/2005 | Foley ................... A61F 2/4455 623/17.11 |
| 2005/0125029 A1 | 6/2005 | Bernard et al. |
| 2005/0149193 A1 | 7/2005 | Zucherman et al. |
| 2005/0154391 A1 | 7/2005 | Doherty et al. |
| 2005/0159813 A1 | 7/2005 | Molz |
| 2005/0159818 A1 | 7/2005 | Blain |

(56) References Cited

U.S. PATENT DOCUMENTS

| | | |
|---|---|---|
| 2005/0159819 A1 | 7/2005 | McCormick et al. |
| 2005/0171606 A1 | 8/2005 | Michelson |
| 2005/0171607 A1 | 8/2005 | Michelson |
| 2005/0177236 A1 | 8/2005 | Mathieu et al. |
| 2005/0216059 A1 | 9/2005 | Bonutti et al. |
| 2005/0222683 A1 | 10/2005 | Berry |
| 2005/0240267 A1 | 10/2005 | Randall et al. |
| 2005/0240271 A1 | 10/2005 | Zubock et al. |
| 2005/0261767 A1 | 11/2005 | Anderson et al. |
| 2005/0267534 A1 | 12/2005 | Bonutti et al. |
| 2006/0020342 A1 | 1/2006 | Ferree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0167495 A1 | 7/2006 | Bonutti et al. |
| 2006/0195189 A1 | 8/2006 | Link et al. |
| 2006/0195193 A1 | 8/2006 | Bloemer |
| 2006/0206208 A1 | 9/2006 | Michelson |
| 2006/0229725 A1 | 10/2006 | Lechmann et al. |
| 2006/0235470 A1 | 10/2006 | Bonutti et al. |
| 2006/0265009 A1 | 11/2006 | Bonutti |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0177236 A1 | 8/2007 | Kijima et al. |
| 2007/0208378 A1 | 9/2007 | Bonutti et al. |
| 2007/0219365 A1 | 9/2007 | Joyce et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1* | 10/2007 | Bray .............. A61F 2/4455 623/17.11 |
| 2007/0270961 A1 | 11/2007 | Ferguson |
| 2008/0033440 A1 | 2/2008 | Moskowitz et al. |
| 2008/0039873 A1 | 2/2008 | Bonutti et al. |
| 2008/0047567 A1 | 2/2008 | Bonutti |
| 2008/0051890 A1 | 2/2008 | Waugh et al. |
| 2008/0058822 A1 | 3/2008 | Bonutti |
| 2008/0065140 A1 | 3/2008 | Bonutti |
| 2008/0082169 A1 | 4/2008 | Gittings |
| 2008/0103519 A1 | 5/2008 | Bonutti |
| 2008/0108916 A1 | 5/2008 | Bonutti et al. |
| 2008/0114399 A1 | 5/2008 | Bonutti |
| 2008/0119933 A1 | 5/2008 | Aebi et al. |
| 2008/0132949 A1 | 6/2008 | Aferzon et al. |
| 2008/0133013 A1 | 6/2008 | Duggal et al. |
| 2008/0140116 A1 | 6/2008 | Bonutti |
| 2008/0140117 A1 | 6/2008 | Bonutti et al. |
| 2008/0161925 A1 | 7/2008 | Brittan et al. |
| 2008/0177307 A1 | 7/2008 | Moskowitz et al. |
| 2008/0188940 A1 | 8/2008 | Cohen et al. |
| 2008/0200984 A1 | 8/2008 | Jodaitis et al. |
| 2008/0234822 A1 | 9/2008 | Govil et al. |
| 2008/0249569 A1 | 10/2008 | Waugh et al. |
| 2008/0249575 A1 | 10/2008 | Waugh et al. |
| 2008/0249622 A1 | 10/2008 | Gray |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0281425 A1 | 11/2008 | Thalgott et al. |
| 2008/0306596 A1 | 12/2008 | Jones et al. |
| 2008/0312742 A1 | 12/2008 | Abernathie |
| 2009/0076608 A1 | 3/2009 | Gordon et al. |
| 2009/0088849 A1* | 4/2009 | Armstrong ............ A61F 2/4455 623/17.16 |
| 2009/0099661 A1 | 4/2009 | Bhattacharya et al. |
| 2009/0105830 A1 | 4/2009 | Jones et al. |
| 2009/0132051 A1 | 5/2009 | Moskowitz et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2010/0305704 A1 | 12/2010 | Messerli et al. |
| 2010/0312346 A1 | 12/2010 | Kueenzi et al. |
| 2011/0087327 A1 | 4/2011 | Lechmann et al. |
| 2011/0118843 A1 | 5/2011 | Mathieu et al. |
| 2011/0137417 A1 | 6/2011 | Lee |
| 2011/0166660 A1 | 7/2011 | Laurence |
| 2011/0230971 A1 | 9/2011 | Donner et al. |
| 2011/0238184 A1 | 9/2011 | Zdeblick et al. |
| 2011/0295371 A1 | 12/2011 | Moskowitz et al. |
| 2012/0010623 A1 | 1/2012 | Bonutti |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1 | 7/2012 | McDonough et al. |
| 2012/0197401 A1 | 8/2012 | Duncan et al. |
| 2012/0215226 A1 | 8/2012 | Bonutti |
| 2012/0215233 A1 | 8/2012 | Cremens |
| 2012/0221017 A1 | 8/2012 | Bonutti |
| 2012/0323330 A1 | 12/2012 | Kueenzi et al. |
| 2013/0073046 A1 | 3/2013 | Zaveloff et al. |
| 2013/0073047 A1 | 3/2013 | Laskowitz et al. |
| 2013/0166032 A1 | 6/2013 | McDonough et al. |
| 2013/0173013 A1 | 7/2013 | Anderson et al. |
| 2013/0226185 A1 | 8/2013 | Bonutti |
| 2013/0237989 A1 | 9/2013 | Bonutti |
| 2013/0268008 A1 | 10/2013 | McDonough et al. |
| 2013/0289729 A1 | 10/2013 | Bonutti |
| 2014/0018854 A1 | 1/2014 | Bonutti et al. |
| 2014/0025110 A1 | 1/2014 | Bonutti et al. |
| 2014/0025111 A1 | 1/2014 | Bonutti et al. |
| 2014/0025112 A1 | 1/2014 | Bonutti |
| 2014/0025168 A1 | 1/2014 | Klimek et al. |
| 2014/0081406 A1 | 3/2014 | Kellar et al. |
| 2014/0100663 A1 | 4/2014 | Messerli et al. |
| 2014/0121777 A1 | 5/2014 | Rosen et al. |
| 2014/0180422 A1 | 6/2014 | Klimek et al. |
| 2014/0214166 A1 | 7/2014 | Theofilos |
| 2014/0228963 A1 | 8/2014 | Bonutti |
| 2014/0243985 A1 | 8/2014 | Lechmann et al. |
| 2014/0257380 A1 | 9/2014 | Bonutti |
| 2014/0257487 A1 | 9/2014 | Lawson et al. |
| 2014/0277456 A1 | 9/2014 | Kirschman |
| 2014/0309560 A1 | 10/2014 | Bonutti |
| 2014/0336770 A1 | 11/2014 | Petersheim et al. |
| 2014/0343573 A1 | 11/2014 | Bonutti |
| 2014/0371859 A1 | 12/2014 | Petersheim et al. |
| 2015/0257893 A1 | 9/2015 | Gamache |
| 2016/0113774 A1 | 4/2016 | Schmura et al. |

FOREIGN PATENT DOCUMENTS

| | | |
|---|---|---|
| CA | 2317791 A1 | 8/1999 |
| CN | 1383790 A | 12/2002 |
| CN | 1620271 A | 5/2005 |
| CN | 1701772 A | 11/2005 |
| CN | 1901853 A | 1/2007 |
| DE | 2821678 A | 11/1979 |
| DE | 3042003 A1 | 7/1982 |
| DE | 3933459 A1 | 4/1991 |
| DE | 4242889 A1 | 6/1994 |
| DE | 4409392 A1 | 9/1995 |
| DE | 4423257 | 1/1996 |
| DE | 19504867 C1 | 2/1996 |
| DE | 29913200 U1 | 9/1999 |
| DE | 202004020209 | 5/2006 |

(56) References Cited

FOREIGN PATENT DOCUMENTS

| | | |
|---|---|---|
| EP | 0179695 | 4/1986 |
| EP | 0302719 A1 | 2/1989 |
| EP | 0505634 A1 | 9/1992 |
| EP | 0517030 B1 | 9/1992 |
| EP | 0517030 A2 | 12/1992 |
| EP | 0517030 A3 | 4/1993 |
| EP | 0577178 A1 | 1/1994 |
| EP | 0639351 A2 | 2/1995 |
| EP | 0425542 B1 | 3/1995 |
| EP | 0639351 A3 | 3/1995 |
| EP | 504346 B1 | 5/1995 |
| EP | 0505634 B1 | 8/1997 |
| EP | 897697 A1 | 2/1999 |
| EP | 0605799 B1 | 4/1999 |
| EP | 0641547 B1 | 5/1999 |
| EP | 0966930 | 12/1999 |
| EP | 0968692 A1 | 1/2000 |
| EP | 0974319 | 1/2000 |
| EP | 0974319 A2 | 1/2000 |
| EP | 1103236 | 5/2001 |
| EP | 1402836 | 3/2004 |
| EP | 1033941 | 8/2004 |
| EP | 0906065 B1 | 9/2004 |
| EP | 1124512 | 9/2004 |
| EP | 1051133 | 10/2004 |
| EP | 1459711 | 7/2007 |
| EP | 1847240 A1 | 10/2007 |
| EP | 1194087 | 8/2008 |
| FR | 2552659 | 4/1985 |
| FR | 2697996 | 5/1994 |
| FR | 2700947 | 8/1994 |
| FR | 2703580 A1 | 10/1994 |
| FR | 2727003 | 5/1996 |
| FR | 2747034 A1 | 10/1997 |
| FR | 2753368 | 3/1998 |
| GB | 157668 A | 1/1921 |
| GB | 265592 A | 8/1927 |
| GB | 2148122 A | 5/1985 |
| GB | 2207607 | 2/1989 |
| GB | 2239482 A | 7/1991 |
| GB | 2266246 A | 10/1993 |
| JP | 03-505416 | 11/1991 |
| JP | 9-280219 | 10/1997 |
| JP | 2006-513752 | 4/2006 |
| RU | 2229271 | 5/2004 |
| RU | 2244527 | 1/2005 |
| RU | 2307625 | 10/2007 |
| SU | 1465040 A1 | 3/1989 |
| WO | WO 88/03417 | 5/1988 |
| WO | WO 88/10100 | 12/1988 |
| WO | 89/09035 A1 | 10/1989 |
| WO | WO 90/00037 | 1/1990 |
| WO | WO 92/01428 | 2/1992 |
| WO | WO 92/06005 | 4/1992 |
| WO | 93/01771 A1 | 2/1993 |
| WO | 95/08964 A2 | 4/1995 |
| WO | 95/15133 A1 | 6/1995 |
| WO | 95/20370 A1 | 8/1995 |
| WO | WO 95/21053 | 8/1995 |
| WO | 95/26164 A1 | 10/1995 |
| WO | 96/40015 A1 | 12/1996 |
| WO | WO 96/39988 | 12/1996 |
| WO | WO 97/20526 | 6/1997 |
| WO | WO 97/23175 | 7/1997 |
| WO | WO 97/25941 | 7/1997 |
| WO | WO 97/25945 | 7/1997 |
| WO | 97/37620 A1 | 10/1997 |
| WO | WO 97/39693 | 10/1997 |
| WO | 98/17208 A2 | 4/1998 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | 99/09896 A1 | 3/1999 |
| WO | WO 1999/009903 | 3/1999 |
| WO | WO 99/27864 | 6/1999 |
| WO | WO 99/29271 | 6/1999 |
| WO | WO 99/32055 | 7/1999 |
| WO | WO 99/38461 | 8/1999 |
| WO | WO 99/38463 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/25706 | 5/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 A1 | 11/2000 |
| WO | WO 00/66045 | 11/2000 |
| WO | WO 00/74607 A1 | 12/2000 |
| WO | 01/03615 A1 | 1/2001 |
| WO | WO 01/08611 | 2/2001 |
| WO | WO 01/56497 A2 | 8/2001 |
| WO | WO 01/62190 | 8/2001 |
| WO | WO 01/80785 | 11/2001 |
| WO | WO 01/56497 A3 | 12/2001 |
| WO | WO 01/93742 A2 | 12/2001 |
| WO | WO 01/95837 A1 | 12/2001 |
| WO | WO 01/56497 B1 | 3/2002 |
| WO | WO 01/93742 A3 | 9/2002 |
| WO | 2004/000177 A1 | 12/2003 |
| WO | WO 2004/069106 | 8/2004 |
| WO | WO 2005/007040 A | 1/2005 |
| WO | WO 2005/020861 | 3/2005 |
| WO | WO 2006/138500 | 12/2006 |
| WO | WO 2007/098288 | 8/2007 |
| WO | WO 2008/014258 | 1/2008 |
| WO | WO 2008/082473 | 7/2008 |
| WO | 2008/102174 A2 | 8/2008 |
| WO | WO 2008/124355 | 10/2008 |
| WO | WO 2008/154326 | 12/2008 |
| WO | WO 2009/064644 | 5/2009 |
| WO | 2009/158319 A1 | 12/2009 |
| WO | WO 2010/054181 | 5/2010 |
| WO | WO 2010/054208 | 5/2010 |
| WO | WO 2012/088238 | 6/2012 |

OTHER PUBLICATIONS

Appendix 1 to Joint Claim Construction Brief; Synthes' Exhibits A-9, in the United States District Court for the District of Delaware Civil Action No. 1:11-cv-00652-LPS, Jun. 8, 2012, 192 pages.

Appendix 2 to Joint Claim Construction Brief; Globus' Exhibits A-F, in the United States District Court for the District of Delaware Civil Action No. 1:11-cv-00652-LPS, Jun. 8, 2012, 146 pages.

Appendix 3 to Joint Claim Construction Brief; Exhibits A-C, in the United States District Court for the District of Delaware Civil Action No. 1:11-cv-00652-LPS, Jun. 8, 2012, 38 pages.

Expert Report of Dr. Domagoj Carie Regarding the Invalidity of U.S. Pat. Nos. 7,846,207, 7,862,616 and 7,875,076, in the United States District Court for the District of Delaware, Civil Action No. 1:11-cv-00652-LPS, Nov. 5, 2012, 149 pages.

Expert Report of John F. Hall, M.D., United States District Court for the District of Delaware, Civil Action No. 1:11-cv-00652-LPS, Dec. 14, 2012, 27 pages.

Expert Report of Paul Ducheyne, Ph.D. Concerning Patent Validity, United States District Court District of Delaware, Civil Action No. 1:11-cv-00652-LPS, Dec. 13, 2012, 155 pages.

Expert Report of Richard J. Gering, Ph.D., CLP in the United States District Court for the District of Delaware, Civil Action No. 1:11-cv-00652-LPS, Dec. 14, 2012, 39 pages.

Joint Claim Construction Brief, in the United States District Court for the District of Delaware, Civil Action No. 1:11-cv-00652-LPS, Jun. 14, 2012, 97 pages.

Jury Trial Demanded, in the United States District Court for the District of Delaware, Case No. 1:11-cv-00652-LPS, filed Jul. 22, 2011, 8 pages.

Jury Verdict Form, United States District Court District of Delaware, Civil Action No. 1:11-cv-00652-LPS, Jun. 14, 2013, 20 pages.

(56) References Cited

OTHER PUBLICATIONS

Memorandum Opinion, United States District Court District of Delaware, Civil Action No. 1:11-cv-00652-LPS, May 7, 2013, 33 pages.
Order, United States District Court District of Delaware, Civil Action No. 1:11-cv-00652-LPS, May 15, 2013, 4 pages.
Order, United States District Court District of Delaware, Civil Action No. 1:11-cv-00652-LPS, May 7, 2013, 7 pages.
Plaintiffs' Responses and Objections to Defendant Globus Medical, Inc.'s First Set of Interrogatories (Nos. 1-11), United States District Court for the District of Delaware, Civil Action No. 1:11-cv-00652-LPS, Nov. 14, 2011, 18 pages.
Plaintiffs' Supplemental Responses and Objections to Defendant Globus Medical Inc.'s Interrogatories Nos. 6-10 and Second Supplemental Responses and Objections to Interrogatory No. 5, United States District Court for the District of Delaware, Civil Action No. 11-cv-652-LPS, Sep. 1, 2012, 12 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Plaintiff's Reply Brief in Support of Plaintiff's Motion for Summary Judgment of No Anticipation by the Kozak and Michelson References", Mar. 21, 2013, 11 pages.
Reply Report of Dr. Domagoj Carie Regarding the Invalidity of U.S. Pat. Nos. 7,846,207, 7,862,616 and 7,875,076, in the United States District Court for the District of Delaware, Civil Action No. 1:11-cv-00652-LPS, Jan. 4, 2013, 81 pages.
Second Expert Report of Wilson C. Hayes, Ph.D., United States District Court for the District of Delaware, Civil Action No. 1:11-cv-00652-LPS, Dec. 14, 2012, 22 pages.
Trial Transcript, United States District Court District of Delaware, Civil Action No. 1:11-cv-00652-LPS, Jun. 10, 2013, 114 pages.
Trial Transcript, United States District Court District of Delaware, Civil Action No. 1:11-cv-00652-LPS, Jun. 11, 2013, 98 pages.
Trial Transcript, United States District Court District of Delaware, Civil Action No. 1:11-cv-00652-LPS, Jun. 12, 2013, 75 pages.
Trial Transcript, United States District Court District of Delaware, Civil Action No. 1:11-cv-00652-LPS, Jun. 13, 2013, 94 pages.
Trial Transcript, United States District Court District of Delaware, Civil Action No. 1:11-cv-00652-LPS, Jun. 14, 2013, 26 pages.
Trial Transcript, United States District Court District of Delaware, Civil Action No. 1:11-cv-00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 7, 2013, 97 pages.
Japanese Patent Application No. 2011-534926: Office Action dated Oct. 30, 2013, 7 pages.
Japanese Patent Application No. 2011-534928: Office Action dated Sep. 30, 2013, 11 pages.
Russian Patent Application No. 2011-1122797: Decision to Grant dated Oct. 9, 2013, 20 pages.
Synthes Spine, "CorticoCancellous ACF Spacer. An allograft space or anterior fusion of the cervical spine," brochure, Musculoskeletal Transplant Foundationm, 2003, 6 pages.
International Patent Application PCT/US2011/066421, International Search Report dated Jun. 14, 2012, 31 pages.
U.S. Appl. No. 60/988,661, filed Nov. 16, 2007, Kueenzi et al.

Synthes Spine, "SynFix-LR System. Instruments and Implants for Stand-Alone Anterior Lumbar Interbody Fusion (ALIF)", Technique Guide dated 2008, pp. 2-40, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Bray Brochure: InterPlate Vertebral Body Replacement.
Bray, "InterPlate Spine Fusion Device: Subsidence Control Without Stress Shielding", Orthopaedic Product News, Sep./Oct. 2006, pp. 22-25.
International Search Report, dated Mar. 20, 2009, for PCT International Application No. PCT/US08/82473, filed Nov. 5, 2008.
Written Opinion, dated Mar. 20, 2009, for PCT International Application No. PCT/US08/82473, filed Nov. 5, 2008.
Chadwick et al., "Radiolucent Structural Materials for Medical Applications," www.mddionline.com/print/238, Jun. 1, 2001, accessed date Jul. 31, 2012, 9 pages.
Jonbergen et al., "Anterior Cervical Interbody Fusion With a Titanium Box Cage: Early Radiological Assessment of Fusion and Subsidence", The Spine Journal 5, Jul. 2005, 645-649.
Marcolongo et al., "Trends in Materials for Spine Surgery", Comprehensive Biomaterials, Biomaterials and Clinical Use, 6.610, Oct. 2011, 21 pages.
Pavlov et al., "Anterior Lumbar Interbody Fusion with Threaded Fusion Cages and Autologous Grafts", Eur. Spine J., Jun. 2000, 9, 224-229.
Schleicher et al., "Biomechanical Comparison of Two Different Concepts for Stand-Alone Anterior Lumbar Interbody Fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
Spruit et al., "The in Vitro Stabilizing Effect of Polyetheretherketone Cages Versus a Titanium Cage or Similar Design for Anterior Lumbar Interbody Fusion", Eur. Spine J., Aug. 2005, 14, 752-758.
International Patent Application No. PCT/CH2003/00089, International Search Report dated Dec. 2, 2003, 3 pages.
International Search Report, completed Aug. 16, 2007 for International Application No. PCT/US2007/005098, filed Feb. 27, 2007.
U.S. Appl. No. 11/199,599: Amendment/Request for Reconsideration after Non-Final Rejection, dated Sep. 29, 2009, 30 pages.
Younger, Morbidity at Bone Graft Donor Sites, 3(3) J. Orth. Trauma, 192-195, 1989.
Wilson, Anterior Cervical Discectomy without Bone Graft, 47(4) J. Neurosurg. 551-555, Oct. 1977.
Whitesides, Lateral Approach to the Upper Cervical Spine for Anterior Fusion, vol. 59, South Med J, 879-883, Aug. 1966.
White, Relief of Pain by Anterior Cervical-Spine Fusion for Spondylosis, 55-A(3) J. Bone Joint Surg. 525-534, Apr. 1973.
Weiner, Spindle Update Lumbar Interbody Cages, 23(5) Spine, 634-640, Mar. 1998.
Watters, Anterior Cervical Discectomy with and without Fusion, 19(20) Spine 2343-2347 Oct. 1994.
Wang, Increased Fusion Rates with Cervical Plating for Two-Level Anterior Cervical Discectomy and Fusion, 25(1) Spine 41-45, Jan. 2000.
Wang, Determination of Cortical Bone Porosity and Pore Size Distribution using a Low Field Pulsed NMR Approach, J. Orthop Res., Mar; 21 (2)312-9 Mar. 2003.
Verbiest H., La Chirurgie Anterieure et Laterale du Rachis Cervical,16(S2) Neurochirurgie 1-212; 1970 (w/Translation).
U.S. Appl. No. 11/199,599: Interview Summary including Draft Claim Amendments dated Sep. 24, 2009, 16 pages.
U.S. Appl. No. 11/199,599: Appeal Brief dated Apr. 15, 2010, 51 pages.
U.S.Provisional Application filed on Sep. 16, 2011 by Jillian Zaveloff, entitled "Multi-Piece Intervertebral Implants", U.S. Appl. No. 61/535,726.
U.S.Provisional Application filed on Jan. 15, 1998 by David J. Urbahns, entitled "Insertion Instruments and Method for Delivering a Vertebral Body Spacer", U.S. Appl. No. 60/071,527.

(56) References Cited

OTHER PUBLICATIONS

U.S.Provisional Application filed on Dec. 19, 1997 by David J. Urbahns et al.,entitled "Insertion Instruments and Method for Delivering a Vertebral Body Spacer", U.S. Appl. No. 60/068,205.
U.S. Appl. No. 11/199,599: Preliminary Amendment, dated Jan. 9, 2008, 11 pages.
U.S. Appl. No. 11/199,599: Non-Final Rejection, dated Apr. 1, 2009, 20 pages.
U.S. Appl. No. 11/199,599: Final Rejection, dated Dec. 24, 2009, 21 pages.
Tan, A Modified Technique of Anterior Lumbar Fusion with Femoral Cortical Allograft, 5(3) J. Ortho. Surg. Tech., 83-93, 1990.
Tamariz, Biodegradation of Medical Purpose Polymeric Materials and Their Impact on Biocompatibility, Chapter 1, Intech-bio degradation Life of Science, 2013; 28 pages.
Takahama, A New Improved Biodegradable Tracheal Prosthesis Using Hydroxy Apatite and Carbon Fiber 35(3) ASAIO Trans, 291-293, Jul.-Sep. 1989.
Synthes Spine Cervical Stand-Alone Devices Presentation Brochure; 2010, 40 pages.
Synthes History and Evolution of LBIF Brochure; Nov. 2015, 30 pages.
Sonntag, Controversy in Spine Care, Is Fusion Necessary After Anterior Cervical Discectomy 21(9) Spine, 1111-1113, May 1996.
Samandouras, A New Anterior Cervical Instrumentation System Combinin an Intradiscal Cage with an Integrated plate, 26(10) Spine, 1188-1192, 2001.
Porex Website, http://www.porex.com/technologies/materials/porous-plastics, Porous Plastic Materials, accessed Aug. 21, 2015, 2 pages.
Polysciences Inc. Info Sheet 2012.
PCT International Application No. PCT/US2009/063529: International Search Report and Written Opinion dated Apr. 14, 2010, 19 pages.
PCB Evolution Surgical Technique Guide 2010.
Nasca, Newer Lumbar Interbody Fusion Techniques, 22(2) J. Surg. Ortho. Advances, 113-117, 2013.
McAfee, Minimally Invasive Anterior Retroperitoneal Approach to the Lumbar Spine, 21 (13) Spine, 1476-1484, 1998.
Malca, Cervical Interbody Xenografl with Plate Fixation, 21 (6) Spine, 685-690, Mar. 1996.
Lyu, Degradability of Polymers for Implantable Biomedical Devices, 10, Int. J. Mol. Sci., 4033-4065, 2009.
Lund, Interbody Cage Stabilisation in the Lumbar Spine, 80-B(2) J Bone Joint Surg., 351-359, Mar. 1998.
Kroppenstedt, Radiological Comparison of Instrumented Posterior Lumbar Interbody Fusion with One or Two Closed-3ox Plasmapore Coated Titanium Cages, 33(19) Spine, 2083-2088, Sep. 2008.
Kozak, Anterior Lumbar Fusion Options, No. 300, Clin. Orth. Rel. Res., 45-51, 1994.
Khan, Chapter 2—Implantable Medical Devices, Focal Controlled Drug Delivery, Advances in Delivery Science and Technology, A.J. Domb and W. Khan (eds.) 2014.
Kastner, Advanced X-Ray Tomographic Methods for Quantitative Charecterisation of Carbon Fibre Reinforced Polymers, 4th Annual Intern. Symposium on NDT in Aerospace, 2012, 9 pages.
Jost, Compressive Strength of Interbody Cages in the Lumbar Spine: the Effect of Cage Shape, Posterior Instrumentation and Bone Density, 7 Eur. Spine J. 132-141, 1998.
Huttner, Spinal Stenosis & Posterior Lumbar Interbody Fusion, No. 193, Clinical Ortho Rel. Res. 103-114, Mar. 1985.
Gunatillake, Biodegradable Synthetic Polymers for Tissue Engineering, vol. 5, Eur. Cells Materials, 1-16, 2003.
Graham, Lateral Extracavitary Approach to the Thoracic and Thoracolumbar Spine, 20(7) Orthopedics, 605-610, Jul. 1997.
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Fuentes, Les Complications de la Chirurgie Par Voie Anterieure du Rachis Cervical, 8(1) Rachis 3-14, 1996 (w/Translation).
Fowler, Complications Associated with Harvesting Autogenous Iliac Bone Graft, 24(12) Am. J. Ortho. 895-904, Dec. 1995.
Fassio, Use of Cervical Plate-Cage PCB and Results for Anterior Fusion in Cervical Disk Syndrome, 15(6) Rachis 355-361, Dec. 2003 Translation.
Enker, Interbody Fusion and Instrumentation, No. 300 Clin. Orth. Rel. Res. 90-101, Mar. 1994.
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Dereymaeker, Nouvelle Cure neuro-Chirurgicale de discopathies Cervicales, 2 Neurochimrgie 226-234; 1956 (w/Translation).
DePuy Motech Surgical Titanium Mesh Brochure; 1998, 13 pages.
Delecrin, Morbidite du Prelevement de Greffons osseux au Niveau des Creh'.:S Iliaques dans la Chirurgie Du Rachis; justification du recours aux substituts osseuz, 13(3) Rachis 167-174, 2001 (w/Translation).
Dabrowski, Highly Porous Titanium Scaffolds for Orthopaedic Applications, J. Biomed Mater. Res. B. Appl. Biomat. Oct;95(1):53-61, 2010.
Cloward, The Anterior Approach for Removal of Ruptured Cervical Disks, vol. 15, J. Neuro. 602-617, 1958.
Cloward, Gas-Sterilized Cadaver Bone Graffts for spinal Fusion Operation , 5(1) Spine 4-10 Jan./Feb. 1980.
Carbon Fiber Composite Ramps for Lumbar Interbody Fusion; Apr. 1997, 2 pages.
Bray, InterPlate Vertebral Body Replacement; website accessed May 4, 2017; http://rsbspine.com/Products.aspx, 2 pages.
Brantigan, Pseudarthrosis Rate After Allograft Posterior Lumbar Interbody Fusion with Pedicle Screw and Plate Fixation , 19(11) Spine 1270-1280, Jun. 1994.
Brantigan, Intervertebral Fusion,Chapter 27, posterior Lumbar Interbody Fusion Using the Lumber Interbody Fusion Cage , 437-466, 2006.
Brantigan, Interbody Lumbar Fusion Using a Carbon Fiber Cage Implant Versus Allograft Bone, 19(13) Spine 1436-1444, 1994.
Brantigan, Compression Strength of Donor Bone for Posterior Lumbar Interbody Fusion, 18(9) Spine 1213-1221, 1993.
Brantigan, A Carbon Fiber Implant to Aid Interbody Lumbar Fusion, 16(6S) Spine S277-S282, Jul. 1991.
Brantigan 1/F Cage for PLIF Surgical Technique Guide; Apr. 1991, 22 pages.
Benezech, L'arthrodese Cervicale Par Voie Anterieure a L'Aide de Plaque-Cage P.C.B., 9(1) Rach is 1, 47, 1997 (w/Translation).
Banward, Iliac Crest Bone Graft Harvest Donor Site Morbidity, 20 (9) Spine 1055-1060, May 1995.
Bailey, Stabilzation of the Cervical Spine by Anterior Fusion, 42-A(4), J. Bone Joint Surg., 565-594, Jun. 1960.
Al-Sanabani, Application of Calcium Phosphate Materials in Dentistry, vol. 2013, Int. J. Biomaterials, 1-12, 2013.
AcroMed Carbon Fiber Interbody Fusion Devices; Jan. 1998, 8 pages.

\* cited by examiner

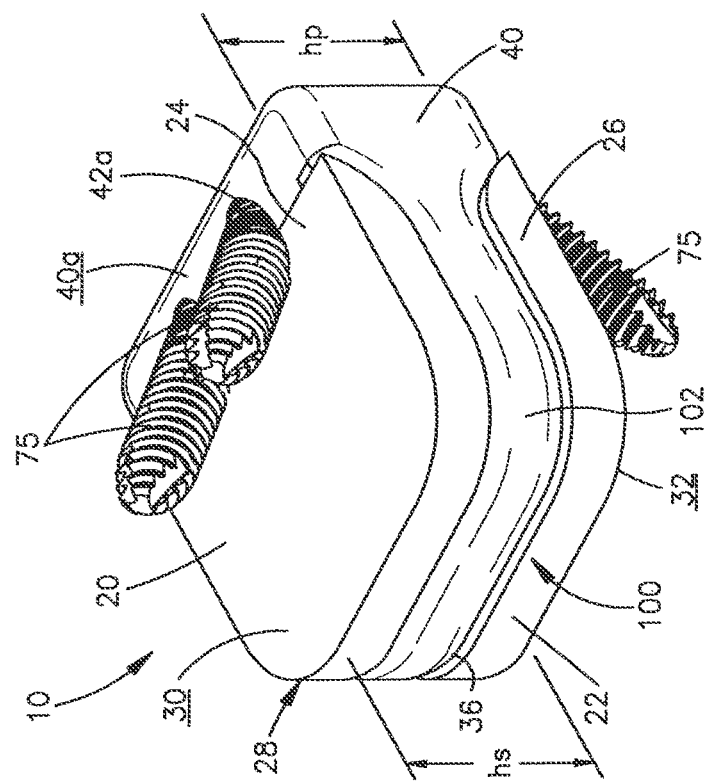
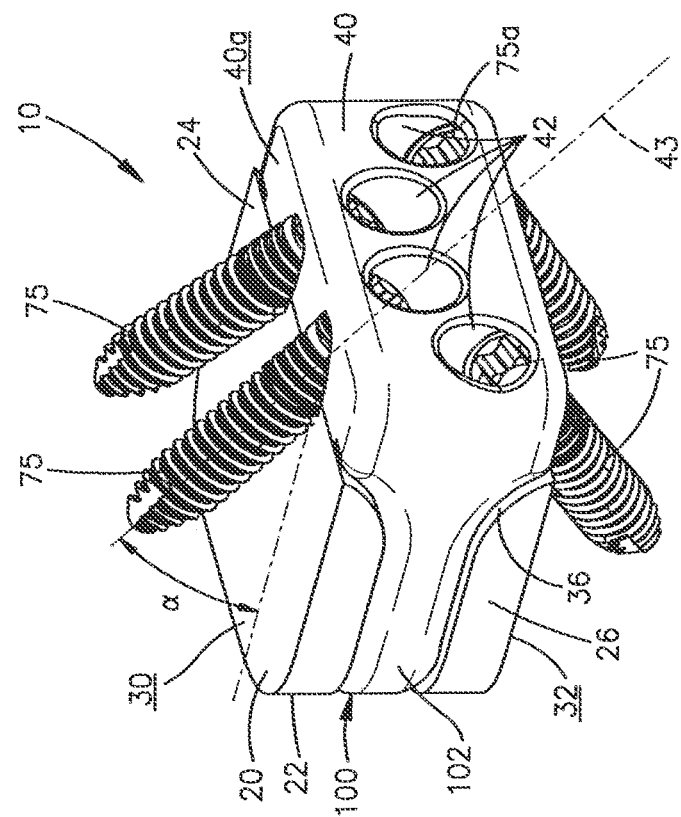
Fig.1A
Fig.1B

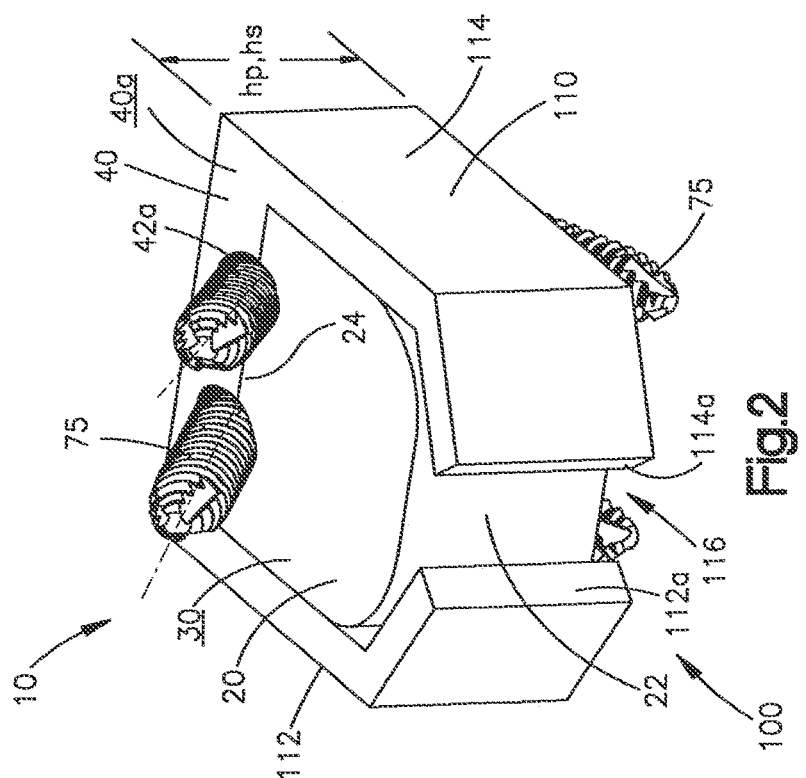

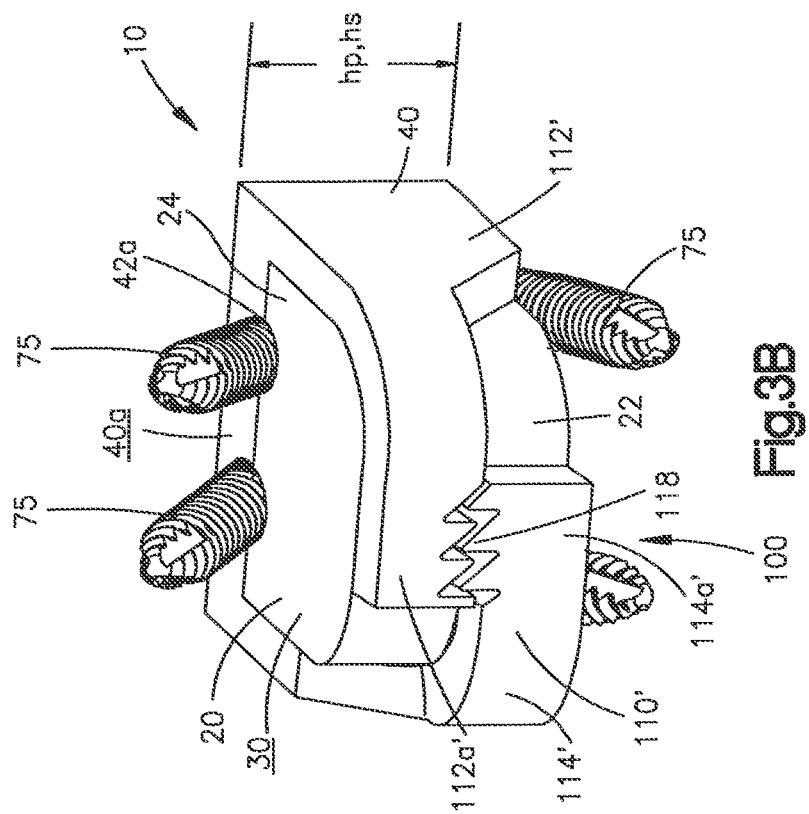
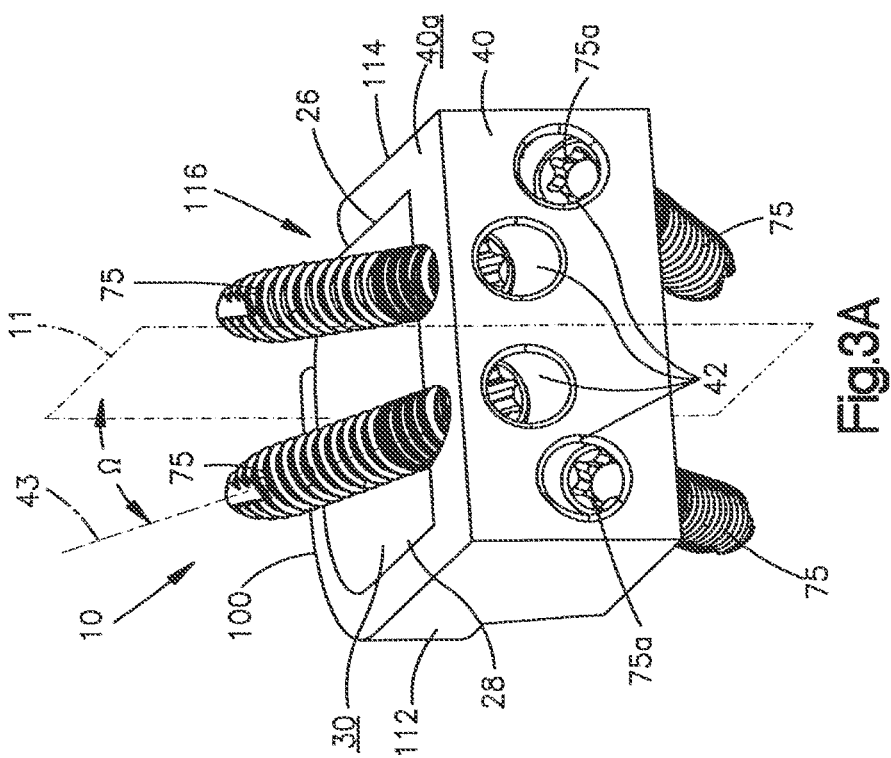
Fig.3A
Fig.3B

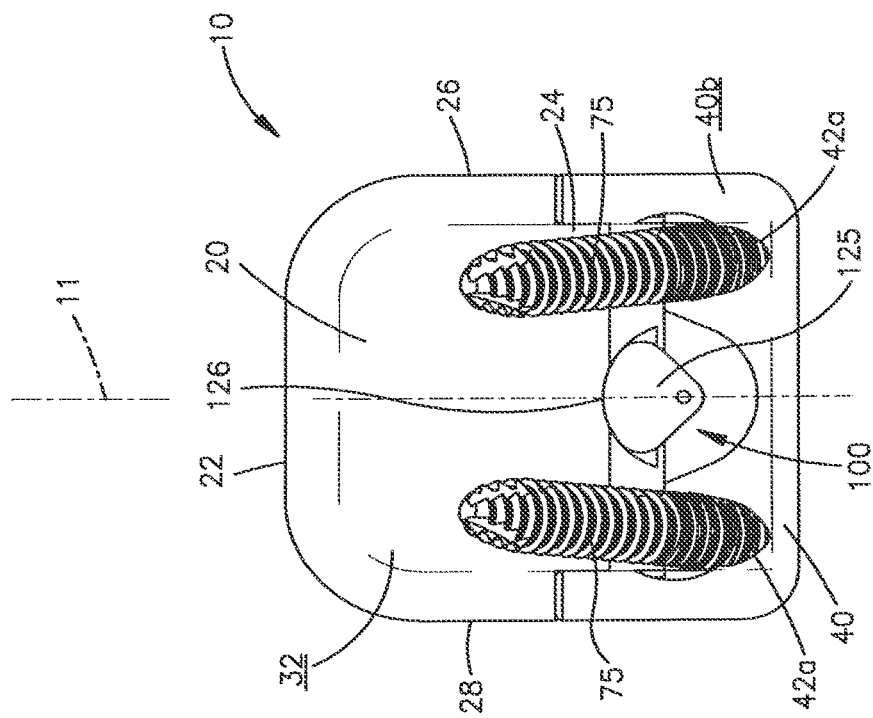
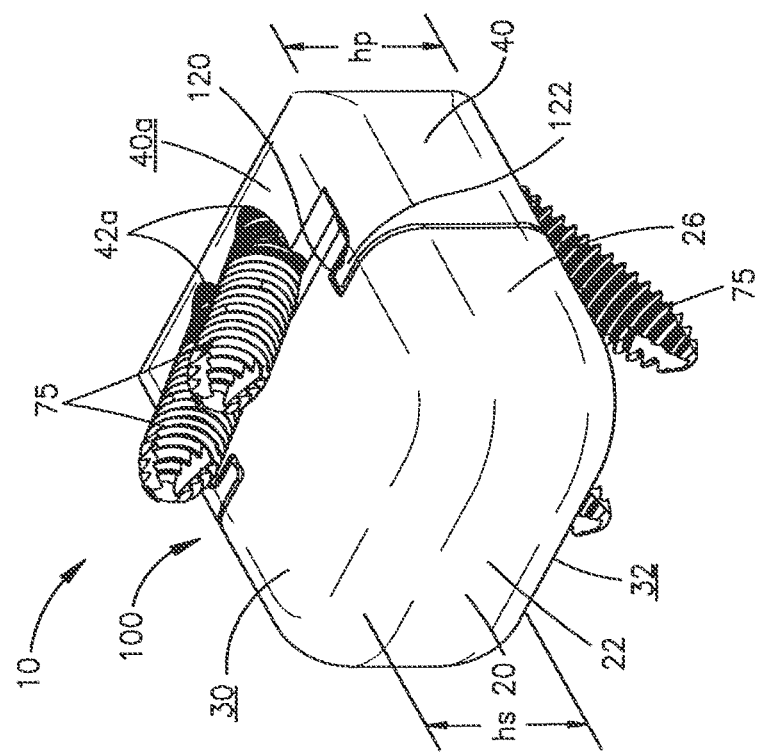

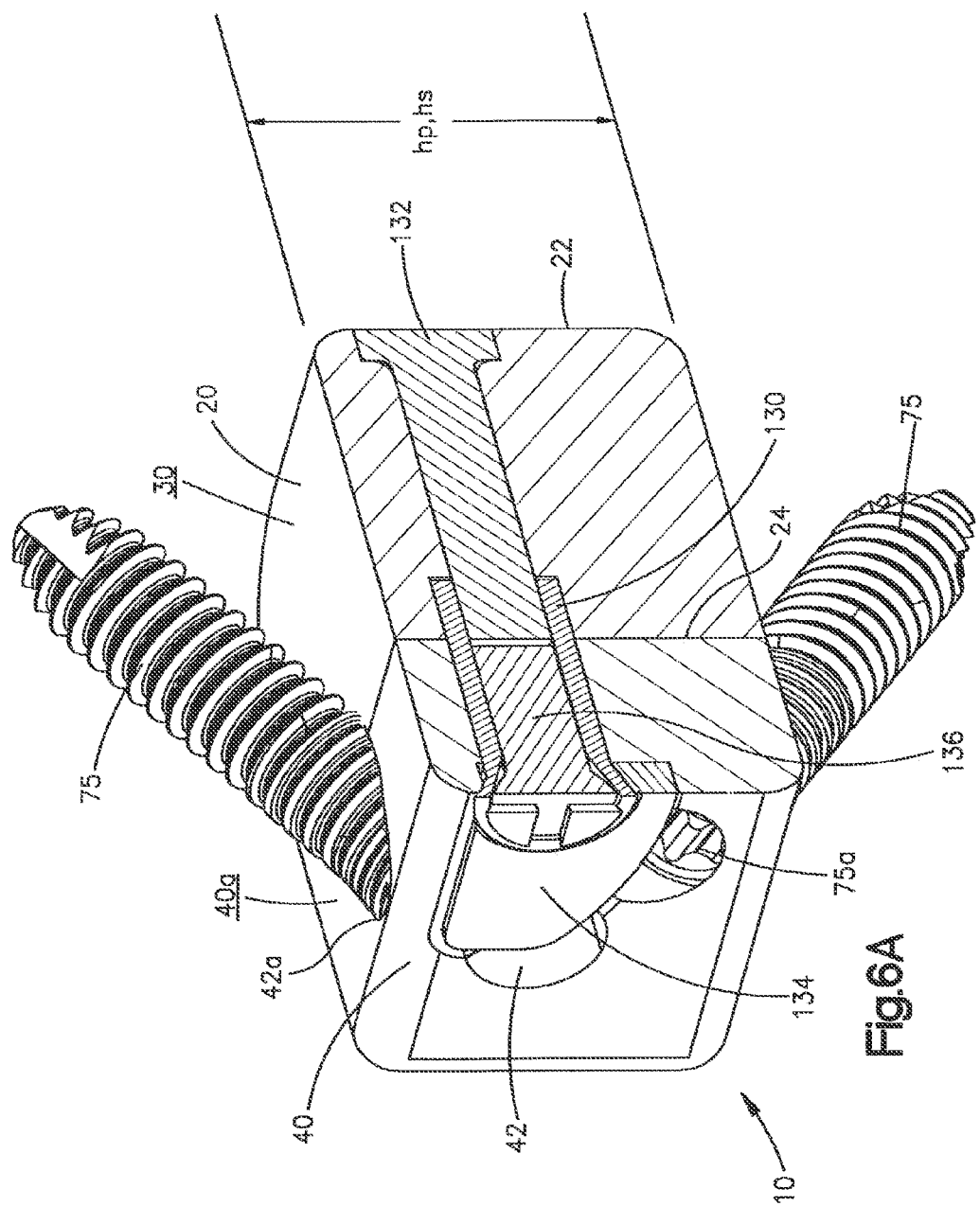

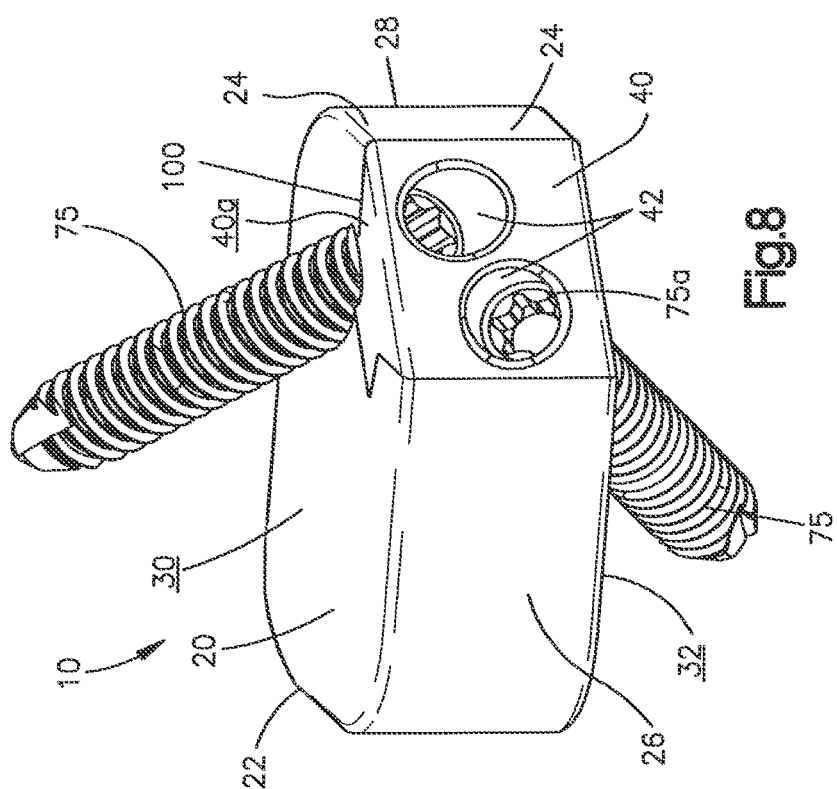
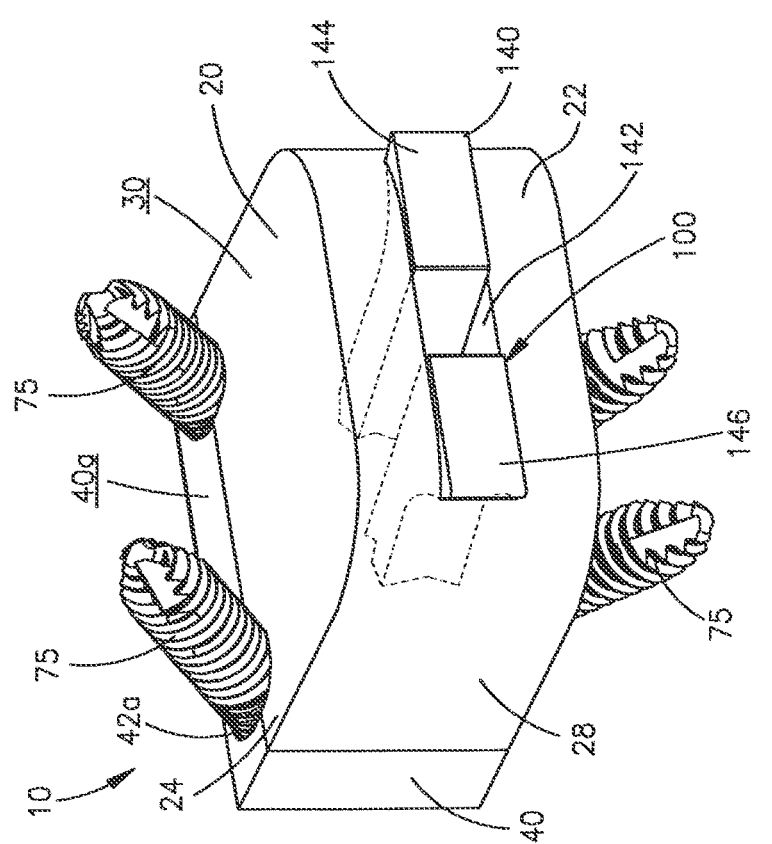

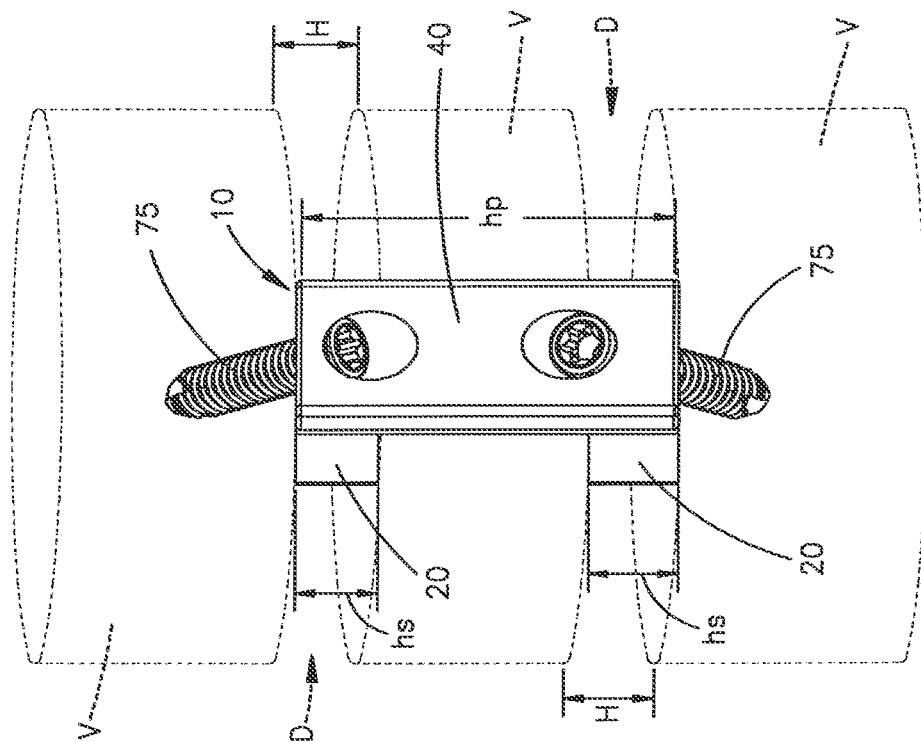
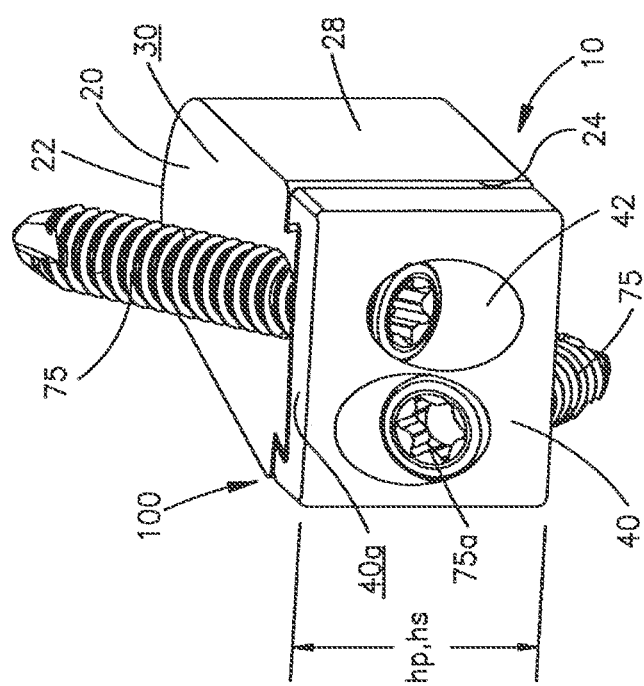

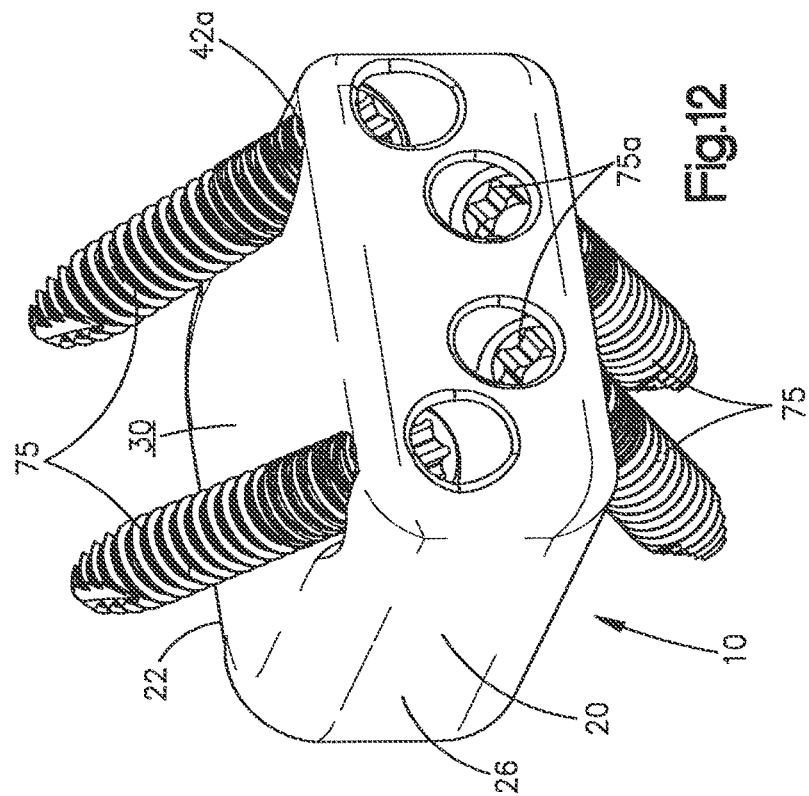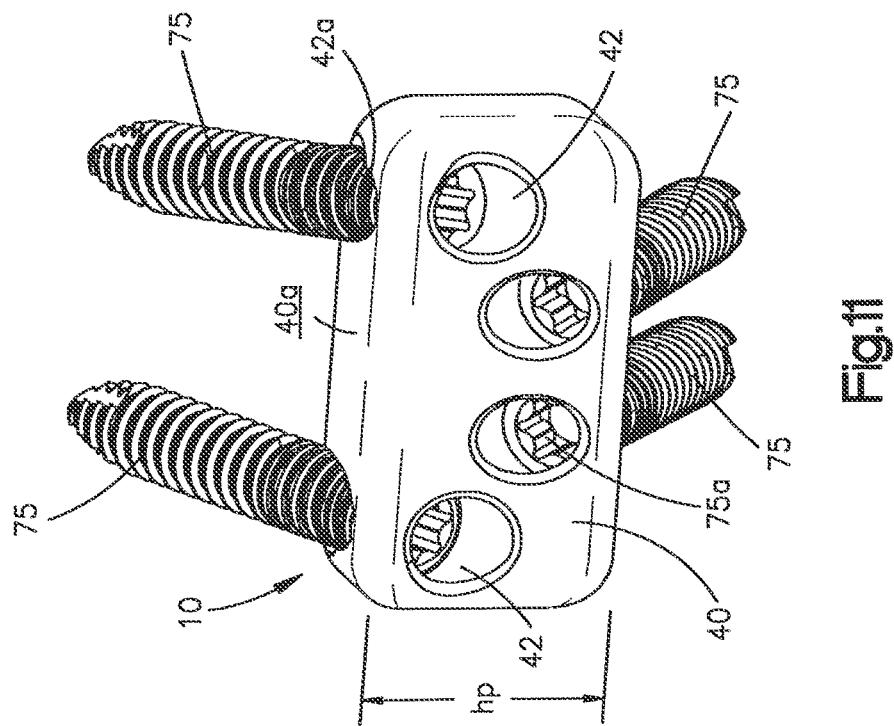

LOW PROFILE INTERVERTEBRAL IMPLANT

CROSS REFERENCE TO RELATED APPLICATIONS

This application is a continuation of U.S. patent application Ser. No. 14/635,480 filed Mar. 2, 2015, which is a continuation of U.S. patent application Ser. No. 13/594,965 filed Aug. 27, 2012, now U.S. Pat. No. 9,005,295 issued Apr. 14, 2015, which is a continuation of U.S. patent application Ser. No. 12/743,098 filed Aug. 25, 2010, now U.S. Pat. No. 8,540,774 issued Sep. 24, 2013, which is a U.S. National Phase of International Application No. PCT/US08/82473 filed Nov. 5, 2008, which claims priority to U.S. Provisional Patent Application No. 60/988,661, filed Nov. 16, 2007, the contents of which are hereby incorporated by reference in their entireties.

FIELD OF THE INVENTION

The present invention relates to an intervertebral implant. More specifically, the preferred embodiment of the present invention relates to a low profile fusion intervertebral implant for implantation into the intervertebral disc space between adjacent vertebral bodies.

BACKGROUND OF THE INVENTION

Millions of people suffer from back pain. In some instances, in order to relieve back pain and/or to stabilize the spinal structure, it becomes necessary to fuse adjacent vertebral bodies at one or more levels. One known method for fusing adjacent vertebral bodies is to implant one or more intervertebral implants into the affected disc space.

SUMMARY OF THE INVENTION

A preferred embodiment of the present invention is directed to a low profile intervertebral implant for implantation in an intervertebral disc space between adjacent vertebral bodies. The intervertebral implant includes a plate preferably coupled to a spacer. The plate is preferably sized and configured so that the plate does not extend beyond the perimeter of the spacer. In this manner, the plate preferably does not increase the height profile of the spacer and the plate may be implanted within the intervertebral disc space in conjunction with the spacer.

In another aspect of the preferred embodiment of the intervertebral implant, the plate is coupled to the spacer by one or more arms extending from the plate. The arms are sized and configured to substantially surround and receive the spacer so that the spacer is securely coupled to the plate. The one or more arms may be a circumferential arm that extends from the plate and which completely wraps around the spacer. The circumferential arm may be sized and configured to shrink as a result of temperature variation. Alternatively, the arms may be a plurality of deformable arms sized and configured to receive the spacer. The arms are preferably deformable to substantially surround and compress against the spacer to secure the spacer to the arms. Alternatively, the one or more arms may be selectively interconnected with one another so that the first and second arms may be placed around the spacer and then tightened to operatively couple the spacer to the plate.

BRIEF DESCRIPTION OF THE DRAWINGS

The foregoing summary, as well as the following detailed description of the preferred embodiments of the application, will be better understood when read in conjunction with the appended drawings. For the purposes of illustrating the preferred intervertebral implants of the present application, there is shown in the drawings preferred embodiments. It should be understood, however, that the application is not limited to the precise arrangements and instrumentalities shown. In the drawings:

FIG. 1A illustrates a rear perspective view of an intervertebral implant in accordance with a first preferred embodiment of the present invention;

FIG. 1B illustrates a top perspective view of the intervertebral implant shown in FIG. 1A;

FIG. 2 illustrates a front perspective view of an intervertebral implant in accordance with a second preferred embodiment of the present invention;

FIG. 3A illustrates a rear perspective view of an intervertebral implant in accordance with a third preferred embodiment of the present invention;

FIG. 3B illustrates a front perspective view of the intervertebral implant shown in FIG. 3A;

FIG. 4A illustrates a top perspective view of an intervertebral implant in accordance with a fourth preferred embodiment of the present invention;

FIG. 4B illustrates a bottom plan view of the intervertebral implant shown in FIG. 4A;

FIG. 6A illustrates a cross-sectional view of the intervertebral implant shown in FIG. 6, taken along line 6a-6a in FIG. 6 with the intervertebral implant in an assembled configuration;

FIG. 7 illustrates a front perspective view of an intervertebral implant in accordance with a seventh preferred embodiment of the present invention;

FIG. 8 illustrates a rear perspective view of an intervertebral implant in accordance with an eighth preferred embodiment of the present invention;

FIG. 9 illustrates a rear perspective view of an intervertebral implant in accordance with an ninth preferred embodiment of the present invention;

FIG. 10 illustrates a rear elevational view of an intervertebral implant in accordance with a tenth preferred embodiment of the present invention, wherein the intervertebral implant is mounted to a spine;

FIG. 11 illustrates a rear perspective view of an intervertebral implant in accordance with an eleventh preferred embodiment of the present invention; and FIG. 12 illustrates a rear perspective view of an intervertebral implant in accordance with a twelfth preferred embodiment of the present invention.

DETAILED DESCRIPTION OF THE INVENTION

Figure 5:
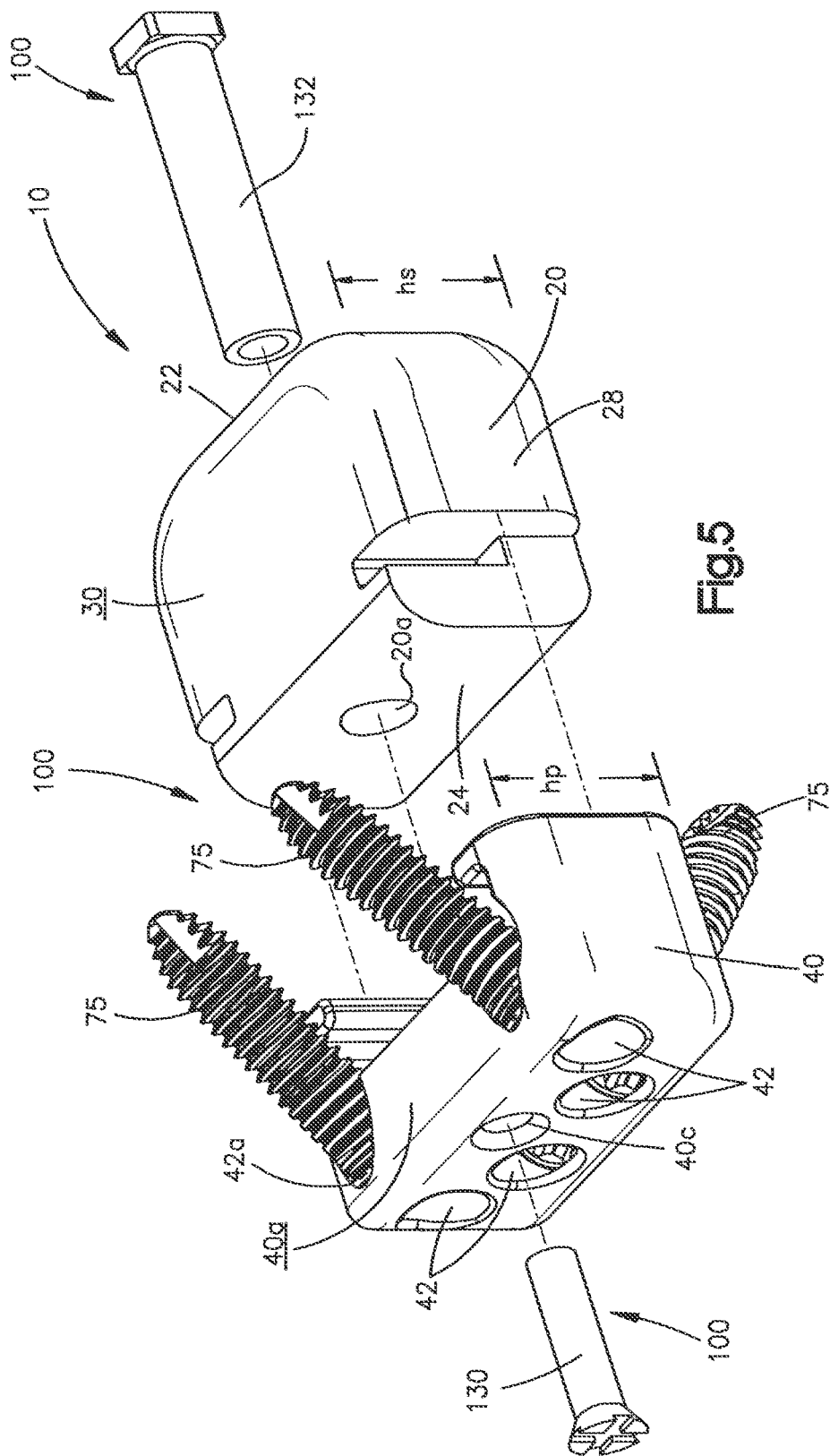
FIG. 5 illustrates a partially exploded top perspective view of an intervertebral implant in accordance with a fifth preferred embodiment of the present invention.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIGS. 1A-12, certain exemplary embodiments of the invention will now be described with reference to the drawings. In general, such embodiments relate to a low profile intervertebral implant 10. It should be understood that while the various embodiments of the intervertebral implant 10 will be described in connection with spinal surgery, those skilled in the art will appreciate that the intervertebral implant 10 as well as the components thereof may be used for implantation into other parts of the body. The same reference numerals will be utilized throughout the application to describe similar or the same components of each of the twelve preferred embodiments of the preferred intervertebral implants described herein and the descriptions will focus on the specific features of the individual embodiments that distinguish the particular embodiment from the others.

Generally speaking, the various embodiments of the intervertebral implant 10 are sized and configured to be implanted between adjacent vertebral bodies V. The intervertebral implants 10 may be sized and configured to replace all or substantially all of an intervertebral disc space D between adjacent vertebral bodies V or only part of the intervertebral disc space D. In addition, the preferred intervertebral implants 10 may be configured to replace an entire vertebral body V and related disc spaces D or multiple disc spaces D in a patient's spine, as is apparent to one having ordinary skill in the art.

The intervertebral implants 10 of each of the preferred embodiments preferably include a plate 40 and a spacer 20. The spacer 20 may include a first insertion end portion 22 (e.g., front end), a second end portion 24 (e.g., rear end) opposite the first insertion end portion 22, a first lateral end 26, a second lateral end 28, an upper surface 30, and a lower surface 32. The spacer 20 is preferably configured and dimensioned for implantation into the intervertebral disc space D between adjacent vertebral bodies V. The spacer 20 is preferably sized and configured to maintain and/or restore a desired intervertebral disc height H between the adjacent vertebral bodies V.

The plate 40 is preferably mounted to the second end portion 24 of the spacer 20 and preferably does not extend beyond the perimeter of the spacer 20. That is, a plate height $h_p$ of the plate 40 is preferably no more than a spacer height $h_s$ of the spacer 20 at the second end 24 so that the plate 40 does not increase the height profile of the spacer 20. In this manner, the intervertebral implant 10 has a low profile. Additionally, in this manner, the plate 40 may be entirely implanted into the intervertebral disc space D between the adjacent vertebral bodies V such that the plate 40 does not extend beyond an edge of the disc space D.

The upper and lower surfaces 30, 32 of the spacer 20 include a series of teeth, one or more keels, or other similar projections (not shown) to aid in securing the intervertebral implant 10 to the endplates of the adjacent vertebral bodies V. Alternatively or in addition, the spacer 20 may include one or more windows or channels (not shown) designed to receive bone graft material. For example, the spacer 20 may include one or more vertical windows or channels (not shown) extending through the spacer 20 from the upper surface 30 to the lower surface 32 for insertion of bone graft material such that bone growth is promoted through the vertical windows or channels following implantation of the intervertebral implant 10. Alternatively or in addition, the spacer 20 may have one or more horizontal windows or channels (not shown) extending through the spacer 20 from the first lateral end 26 to the second lateral end 28 for receiving bone graft material.

The upper and lower surfaces 30, 32 of the spacer 20 may include a curved or a tapered surface to help provide the proper shape to the spine or to orient the endplates of the adjacent vertebral bodies V in a desired manner. The particular surface shape and curvature or taper in the anterior-posterior direction as well as between the first and second lateral ends 26, 28 will depend upon the location the implant 10 is intended to be implanted and/or surgeon preferences.

The intervertebral implant 10 may be constructed of any suitable material or combination of materials including, but not limited to polymer (e.g. PEEK), titanium, titanium alloy, stainless steel, Nitinol, tantalum nitride (TaN), allograft bone, bioresorbable material, magnesium, composites, synthetic bone-welding polymers, etc. The plate 40 may be formed of a different material than the spacer 20. For example, the plate 40 may be formed of a metallic material such as, for example, a titanium or a titanium alloy, and the spacer 20 may be formed of a non-metallic material such as, for example, an allograft, a polymer, a bioresorbable material, a ceramic, etc. Alternatively, the plate 40 and the spacer 20 may be formed from the same material. For example, the plate 40 and the spacer 20 may both be constructed of tantalum nitride (TaN).

The plate 40 preferably includes one or more through holes 42 for receiving fasteners 75 such as, for example, one or more bone screws 75, for securing the intervertebral implant 10 to the adjacent vertebral bodies V. The plate 40 may include any number of through holes 42 arranged in any number of combinations. For example, the plate 40 may include two, three, four or more through holes 42 for receiving, preferably, an equal number of bone screws 75. Moreover, the through holes 42 may alternate with one another with one through hole 42 being angled up and the next through hole 42 being angled down (FIGS. 8 and 9), or the through holes 42 on the outside may be angled up while the through holes 42 on the inside may be angled down (FIGS. 5-7, 11 and 12), etc.

The plate 40 of the preferred embodiments includes at least two through holes 42 configured to receive two fasteners 75 for securing the intervertebral implant 10 to the adjacent vertebral bodies V. The at least two through holes 42 preferably diverge so that at least one fastener 75 is secured into the upper vertebral body V while at least one other fastener 75 is secured into the lower vertebral body V so that opposing forces act on the plate 40 and/or vertebral bodies V. Alternatively, the plate 40 may include three through holes 42 configured to receive three fasteners 75. One fastener 75 may penetrate the upper vertebral body V and two fasteners 75 may penetrate the lower vertebral body V, or vice versa. Alternatively, the plate 40 may include four or more through holes 42 configured to receive four or more fasteners 75. In such a configuration, two inner fasteners 75 may penetrate the upper vertebral body V while two outer fasteners 75 may penetrate the lower vertebral body V, or vice versa, or some combination thereof.

The through holes 42 each include a hole axis 43 such that one of the holes 42 exit through the upper surface of the intervertebral implant 10, possibly through the upper surface 30, for engaging the upper vertebral body V while another of the holes 42 exit through the lower surface of the intervertebral implant 10, possibly through the lower surface 32 for engaging the lower vertebral body V. The fastener 75 that extends through the hole 42, preferably along the hole axis 43 forms a fastener angle α with respect to the upper and lower surfaces 30, 32 of the spacer 20 wherein fastener angle α may be in the range between twenty degrees (20°) and fifty degrees (50°), and most preferably between thirty degrees (30°) and forty-five degrees (45°). The fastener angle α may be the same for all of the holes 42 or may be different for each of the holes 42.

The through holes 42 formed in the plate 40 preferably are directed outwardly from the center of the intervertebral implant 10, preferably at a lateral fastener angle Ω. Thus, the through holes 42 preferably extend laterally outward from a center plane 11 of the intervertebral implant 10 at the lateral fastener angle Ω. The lateral fastener angle Ω may be the same for all holes 42 or may be different for each hole 42.

Exit openings 42a of the through holes 42 may be formed in the plate 40 or in the spacer 20. The through holes 42 may also include one or more threads (not shown) for threadably engaging threads formed on a head portion 75a of the bone screw 75 in order to secure the bone screws 75 to the plate 40 and to generally lock the position of the bone screws 75 relative to the plate 40 and/or spacer 20.

The intervertebral implant 10 of the preferred embodiments also preferably includes a coupling mechanism 100 for securing the plate 40 to the spacer 20. Generally speaking, the spacer 20 and the plate 40 are coupled together by the coupling mechanism 100 prior to being implanted into the disc space D. However, in certain embodiments, the intervertebral implant 10 may be configured so that the plate 40 may be coupled to the spacer 20 after one of the spacer 20 and plate 40 have been implanted into the intervertebral disc space. Once coupled, the spacer 20 and plate 40 preferably form a solid implant. The coupling mechanism 100 may be any of the coupling mechanisms 100 described herein or their structural equivalents.

Referring to a first preferred embodiment of the intervertebral implant 10 shown in FIGS. 1A and 1B, the coupling mechanism 100 may be in the form of a solid, circumferential arm 102 that extends from the plate 40. The circumferential arm 102 is preferably sized and configured to wrap around and/or to receive the spacer 20 therein. Preferably, the spacer 20 includes a recess 36 formed on the outer surfaces thereof for receiving at least a portion of the circumferential arm 102.

The circumferential arm 102 may be made from a material that deforms or shrinks as a result of being heated or cooled such as, for example, Nitinol or any other suitable material that deforms as a result of temperature variation. In this manner, the plate 40 may be fixed to the spacer 20 by heating or cooling the plate 40, thereby causing the arm 102 of the plate 40 to shrink, which in turn causes the arm 102 to circumferentially engage the spacer 20. This first preferred embodiment of the intervertebral implant 10 is particularly useful since it enables relatively loose tolerances during manufacturing of the spacer 20.

Referring to a second preferred embodiment of the intervertebral implant 10 shown in FIG. 2, the coupling mechanism 100 may be in the form of a split ring 110. That is, the plate 40 may include a pair of arms 112, 114 extending therefrom, wherein the arms 112, 114 are sized and configured to substantially surround the outer circumference of the spacer 20 in order to couple the spacer 20 to the plate 40. The arms 112, 114 are preferably configured so as to be deformable around the spacer 20. That is, the arms 112, 114 are preferably able to deform so that the arms 112, 114 can wrap around and/or squeeze the spacer 20. The intervertebral implant 10 of the second preferred embodiment is not limited to having the pair of arms 112, 114 and may include nearly any number of arms extending from the plate 40 that are deformable to engage and secure the spacer 20 relative to the plate 40.

As best shown in FIG. 2, the split ring 110 may be include an open gap 116 proximate the first insertion end portion 22 of the implant 10 that defines terminal ends 112a, 114a of the arms 112, 114. The end portions of the arms 112, 114 proximate the terminal ends 112a, 114a are preferably deformable to permit manual clamping of the spacer 20 with the arms 112, 114 to secure the spacer 20 to the plate 40. The gap 116 is not limited to being positioned generally along a midline of the spacer 20 opposite the plate 40 and may be located at nearly any position relative to the plate 40 that permits the arms 112, 114 to deform and clamp or otherwise secure the spacer 20 to the plate 40. For example, the gap 116 may be positioned proximate a corner of the preferred spacer 20 proximate an intersection of the first insertion end portion 22 and one of the first and second lateral ends 26, 28.

Referring to FIGS. 3A and 3B, in a third preferred embodiment of the intervertebral implant 10, the split ring 110' may be sized and configured so that the arms 112', 114' may be interconnected to one another at their terminal ends 112a', 114a' so that, in use, the split ring 110' may be placed around the spacer 20 and then tightened to operatively couple the plate 40 to the spacer 20. The interconnected arms 112', 114' of the split ring 110' of the third preferred embodiment may be tighten by any means including but not limited to a ratcheting locking mechanism 118, a hose clamp design, etc. Incorporation of the split ring 110' of the third preferred embodiment enables the plate 40 to accommodate spacers 20 of variable dimensions and compositions. Furthermore, incorporation of the split ring 110' of the third preferred embodiment may enable the intervertebral implant 10 to be assembled in situ. Other, alternate designs of the plate 40 that allow for the coupling of the plate 40 around the spacer 20 are envisioned. Alternatively, incorporation of the split ring 110' of the third preferred embodiment may enable the surgeon to incorporate bone packing material as opposed to a pre-formed spacer 20 as described herein and as would be apparent to one having ordinary skill in the art.

Referring to the fourth preferred embodiment of the intervertebral implant 10 shown in FIGS. 4A and 4B, the coupling mechanism 100 may be in the form of a recess 120 preferably extending from the upper surface 30 to the lower surface 32 of the spacer 20 to engage a projection 122 formed on and extending from the plate 40 in an assembled configuration. The recess 120 may be formed in the first and second lateral ends 26, 28 of the spacer 20, in only one of the first and second lateral ends 26, 28, centrally within the spacer 20 or otherwise formed for engagement by the projection 122. For example, as shown, the coupling mechanism 100 of the fourth preferred embodiment is in the form of a dovetail joint, wherein the recess 120 is comprised of recesses 120 extending from the top surface 30 toward the bottom surface 32 proximate the second end 24 and the first and second lateral ends 26, 28, respectively. In this fourth preferred embodiment, the coupling mechanism 100 preferably enables the plate 40 to unidirectionally, slidably engage the spacer 20 by sliding the projection 122 into the recess 120, wherein the projection 122 and recess 120 are formed to prevent the spacer 20 from being engaged with the plate 40 unless the spacer 20 is aligned with the plate 40 and slides along a unitary engagement direction. Alternatively, the projection 122 formed on the plate 40 may be sized and configured to flex across the spacer 20 until the projections 122 substantially fit inside the recesses 120 thereby coupling the spacer 20 to the plate 40 via a press-fit arrangement. It should be appreciated that the locations of the projections 122 and the recesses 120 may be reversed so that the spacer 20 includes the projections and the plate 40 includes the recesses, respectively. In addition, the projections 122 and recesses 120 are preferably sized to align the spacer 20 with the plate 40 such that the top surface 30 of the spacer 20 is generally coplanar with a top surface 40a of the plate 40 and a bottom surface 32 of the spacer 20 is generally coplanar or aligned with a bottom surface 40b of the plate 40 in the assembled configuration. Specifically, the projections 122 and the recesses 120 may be tapered to promote the unitary insertion of the spacer 20 into engagement with the plate 40 and alignment of the top and bottom surfaces 40a, 40b of the plate 40 with the top and bottom surfaces 30, 32 of the spacer 20 in the assembled configuration.

In addition, the coupling mechanism 100 of the fourth preferred embodiment may include one or more rotatable cams 125, preferably coupled to the plate 40 to lock the spacer 20 to the plate 40 after the spacer 20 is slid onto the plate 40. Alternatively, the one or more rotatable cams 125 may act as a depth stop to prevent the plate 40 and the spacer 20 from sliding completely past one another as the spacer 20 slides onto the plate 40 to engage the projections 122 with the recesses 120, respectively. The cam 125 may be included on either or both of the upper and lower surfaces of either or both of the plate 40 and spacer 20. Preferably, for example, the plate 40 may include one or more cams 125 on the upper and lower surfaces of the plate 40, wherein the cam 125 is sized and configured to engage one or more recesses 126 formed on the upper and lower surfaces 30, 32 of the spacer 20. In use, the plate 40 and the spacer 20 may be coupled to each other by rotation of the cam 125, which may be accomplished by hand or with the benefit of a tool.

Figure 6:
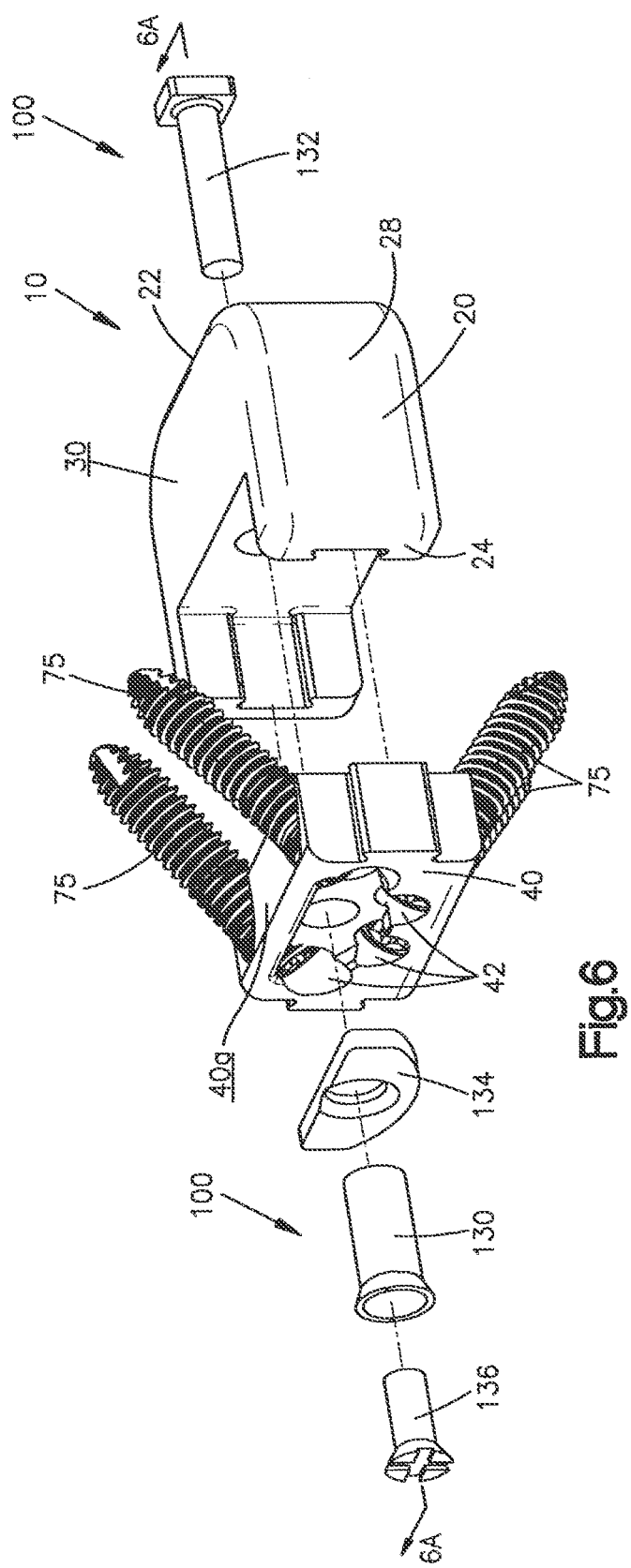
FIG. 6 illustrates a partially exploded side perspective view of an intervertebral implant in accordance with a sixth preferred embodiment of the present invention.

Referring to the fifth preferred embodiment of the intervertebral implant 10 shown in FIG. 5, the coupling mechanism 100 may include a screw 130 that is sized and configured to mate with a nut or barrel threaded pin 132 through first and second holes 20a, 40c in the spacer 20 and the plate 40, respectively. The screw 130 preferably is sized and configured to mate with the nut or barrel threaded pin 132, which may be inserted from the opposite side of the intervertebral implant 10 to secure the spacer 20 to the plate 40. In use, the screw 130 is threadably engaged to the nut or barrel threaded pin 132, thereby coupling the spacer 20 to the plate 20. As best shown in FIGS. 6 and 6A in a sixth preferred embodiment of the intervertebral implant 10, the screw 130' may be cannulated to allow inclusion and use of a blocking plate 134 and a set screw 136 to prevent "backing-out" of the fasteners 75.

Referring to the seventh preferred embodiment of the intervertebral implant 10 shown in FIG. 7, the coupling mechanism 100 may be in the form of a swag plate 140 that extends into and engages the distal end of an aperture 142 formed in the spacer 20. The plate 40 comprises two arms 144, 146 in the preferred embodiment that extend from the plate 40 into the aperture 142. In use, the arms 144, 146 may be urged together at their distal ends and inserted into the aperture 142 until the ends of the arms 144, 146 extend through the aperture 142, at which point, the arms 144, 146 are released so that the ends of the arms 144, 146, preferably protrusions formed thereon, engage the distal end of the aperture 142 of the spacer 20. The arms 144, 146 are able to flex or bend proximate their root or proximal ends such that the distal ends of the arms 144, 146 are able to slide through the aperture 142 during assembly. This embodiment enables the plate 40 to engage the spacer 20 from the inside out. In use, this embodiment enables a relatively simple assembly that permits visualization of the anterior/posterior depth of the implant 10 on an X-ray and assembly of the implant 10 in the operating room.

Referring to the eighth preferred embodiment of the intervertebral implant 10 shown in FIG. 8, the spacer 20 may have a generally rectangular or square-shape with the plate 40 mounted proximate a corner of the spacer 20. The plate 40 may be coupled to the spacer 20 by any coupling mechanisms 100 now or hereafter known for such purpose including those described herein. In use, coupling the plate 40 to a corner of the spacer 20, as opposed to one of the long ends, facilitates implanting of the intervertebral implant 10 into the disc space via an oblique angle. This embodiment is preferably used in cervical applications to limit distract the esophagus, via the approach.

Referring to the ninth preferred embodiment of the intervertebral implant 10 shown in FIG. 9, the intervertebral implant 10 includes a relatively narrow lateral footprint. In use, incorporating a narrower lateral footprint enables the intervertebral implant 10 to accommodate smaller sized patients and/or permits smaller incisions to facilitate minimally invasive techniques. The intervertebral implant 10 of the ninth preferred embodiment may be used as a strut so that the remainder of the area around the implant 10 may be packed with bone chips, putty, bone cement, etc. The intervertebral implant 10 of the ninth preferred embodiment may also enable a transpedicular posterior approach. The intervertebral implant 10 may be used for corpectomy as well as discectomy. It should be noted that any of the embodiments disclosed herein may be sized and configured to include a narrower lateral footprint.

Alternatively and/or in addition, as best shown in FIG. 10, a tenth preferred embodiment of the intervertebral implant 10 includes the plate 40 mounted to two spacers 20 such that the implant 10 is able to span one or more vertebral bodies V.

Referring to the eleventh preferred embodiment of the intervertebral implant 10 shown in FIG. 11, the plate 40 may be implanted between adjacent vertebral bodies without a spacer 20 coupled thereto so that the plate 40 may be implanted between adjacent vertebral bodies to maintain the height of the disc space while leaving the surgeon the option as to whether or not to insert an uncoupled spacer 40, bone chips, bone cement, etc. into the remaining portion of the intervertebral disc space D.

The various coupling mechanisms 100 disclosed herein may also include an adhesive bonding for additional coupling of the plate 40 to the spacer 20. That is, various methods of bonding the spacer 20 to the plate 40 may be used in connection with the various coupling mechanisms 100 disclosed herein. These methods, may include, but are not limited to, chemical bonding or process, ultrasound, ultraviolet light, adhesives, bone welding, clamping etc. These methods may be used in addition, or instead of other coupling mechanisms 100.

Furthermore, referring to a twelfth preferred embodiment of the intervertebral implant 10 shown in FIG. 12, the intervertebral implant 10 may be constructed completely of a monolithic material and has angled bores and fasteners 75. The implant 10 and the fasteners 75 are preferably constructed of the same material, which may be, but is not limited to PEEK, titanium, a resorbable polymer, or magnesium. The implant 10 of the twelfth preferred embodiment may be constructed exclusively of a resorbable material that completely resorbes into a patient's body following implantation. Preferably, the intervertebral implant 10 of the twelfth preferred embodiment is made from an allograft material. The intervertebral implant 10 of the twelfth preferred embodiment may be constructed such that the fasteners 75 are formed from synthetic bone material, which may be inserted and thereafter welded to the adjacent vertebral bodies V to thereby couple the intervertebral implant 10 to the adjacent vertebral bodies V. Alternatively, the synthetic bone material fasteners 75 may be constructed without threads in the form of pins. Such synthetic bone fasteners 75 may be non-threaded or include, for example, push-out resistant Christmas tree threads or other types of threads. Incorporation of synthetic bone material fasteners 75 facilitates manufacturing of the intervertebral implant 10 by eliminating metallic components from the implant 10, thereby enabling constructions using exclusively allograft or resorbable materials.

Alternatively, the intervertebral implant 10 of the twelfth preferred embodiment may incorporate a plate 40 coupled to the spacer 20 and welded to the synthetic bone material fasteners 75 by, for example, ultrasound, thereby eliminating the need for any mechanical locking mechanism when the fasteners are mounted in the through holes 42 in an implanted position. In use, manufacturing the spacer 20 from an allograft or resorbable material and incorporating synthetic bone material fasteners 75 results in only the plate remaining within the patient, if any component of the implant 10 remains within the patient, due to the materials resorbing into the patient's body. It should be noted, however, that it is envisioned that synthetic bone material fasteners 75, which may be welded in-situ to the adjacent vertebral bodies V, may be used in connection with any of the intervertebral implants 10 now or hereafter known including any of the various embodiments of the implant 10 described herein.

The intervertebral implants 10 of each of the twelve preferred embodiments are generally sized and configured for anterior insertion, although different configurations may be possible for lateral, antero-lateral or posterior approaches. In addition to the features described, the intervertebral implant 10 may include threaded holes, slots or channels to mate with instruments to facilitate manipulation and insertion.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art. For example, the present invention may be employed in different sections of the spinal column, including, but not limited to, the cervical area.

The invention claimed is:

1. A plate configured to be coupled to a spacer to form an intervertebral implant that is insertable into an intervertebral disc space defined by a first vertebral body and a second vertebral body, the plate comprising:

a body portion including a first surface and a second surface offset from the first surface in a first direction, the body portion defining a first hole having a first entry opening with an enclosed shape defined by the first surface and a first exit opening defined at least partially by the second surface, at least a portion of the first exit opening offset from the first entry opening with respect to a second direction that is oblique to the first direction such that the first hole is configured to receive a bone fixation element that secures the plate to one of the first vertebral body and the second vertebral body, the body portion defining a second hole having a second entry opening with an enclosed shape defined by the first surface and a second exit opening defined at least partially by the second surface, at least a portion of the second exit opening offset from the second entry opening with respect to a third direction that is oblique to the first direction such that the second hole is configured to receive a bone fixation element that secures the plate to the other of the first vertebral body and the second vertebral body, the body portion further including a top surface and a bottom surface, the bottom surface offset from the top surface in a fourth direction that is perpendicular to the first direction, the top surface configured to abut the first vertebral body when the intervertebral implant is inserted into the intervertebral disc space, and the bottom surface configured to abut the second vertebral body when the intervertebral implant is inserted into the intervertebral disc space, wherein an entirety of both the first entry opening and the second entry opening are positioned between the top surface and the bottom surface;

a first arm that extends from the body portion and terminates at a first end such that a portion of the first arm is offset from the second surface in the first direction, the portion of the first arm including a first arm top surface and a first arm bottom surface offset from the first arm top surface in the fourth direction, wherein the first end comprises a first plurality of teeth that are linearly arranged and disposed between the top and bottom surfaces of the body portion; and a second arm that extends from the body portion and terminates at a second end such that a portion of the second arm is offset from the second surface in the first direction, and the second end comprises a second plurality of teeth that face the first plurality of teeth, are linearly arranged, and are disposed between the top and bottom surfaces of the body portion, wherein respective terminal surfaces of the first and second ends are spaced from each other by a distance measured in a fifth direction that is perpendicular to both the first direction and the fourth direction, wherein the first arm and the second arm are sized and configured to securely receive and couple the spacer to the plate, the body portion defines a first height measured from the top surface of the body portion to the bottom surface of the body portion in the fourth direction, the portion of the first arm defines a second height measured from the first arm top surface to the first arm bottom surface in the fourth direction, and the first height is greater than the second height, and wherein at least a portion of the first entry opening is aligned with at least a portion of the second entry opening with respect to the fifth direction.

2. The plate of claim 1, wherein the first height is measured along the first surface, the first arm extends from the second surface in the first direction, the first arm projects inward toward the second arm so as to define the first end of the first arm, and the second height is measured at the first end of the first arm.

3. The plate of claim 1, wherein the first height is a maximum height of the body portion, and the second height is a minimum height of the first arm.

4. The plate of claim 3, wherein the portion of the second arm includes a second arm top surface and a second arm bottom surface offset from the second arm top surface in the fourth direction, the portion of the second arm defines a third height measured from the second arm top surface to the second arm bottom surface in the fourth direction, and the first height is greater than the third height.

5. The plate of claim 4, wherein when the plate is coupled to the spacer, the intervertebral implant is configured to be inserted in the intervertebral disc space such that the second arm top surface faces the first vertebral body and the second arm bottom surface faces the second vertebral body.

6. The plate of claim 5, wherein when the plate is coupled to the spacer, the intervertebral implant is configured to be inserted in the intervertebral disc space such that the second arm top surface abuts the first vertebral body and the second arm bottom abuts the second vertebral body.

7. The plate of claim 5, wherein the second height is equal to the third height.

8. The plate of claim 5, wherein the third height is a minimum height of the second arm.

9. The plate of claim 5, wherein the top surface, the first arm top surface, and the second arm top surface each are configured to face the first vertebral body when the plate is coupled to the spacer and the intervertebral implant is inserted in the intervertebral disc space, and the bottom surface, the first arm bottom surface, and the second arm bottom surface each are configured to face the second vertebral body when the plate is coupled to the spacer and the intervertebral implant is inserted in the intervertebral disc space.

10. The plate of claim 5, wherein the first arm includes a first sidewall and a second sidewall that is opposite the first sidewall, the second arm includes a first sidewall that faces the first sidewall of the first arm, the second arm further includes a second sidewall opposite the first sidewall of the second arm, and the second sidewall of the first arm converges toward the second sidewall of the second arm as the first arm extends in the first direction.

11. The plate of claim 5, wherein both the portion of the first arm and the portion of the second arm are offset from the first exit opening in the first direction.

12. The plate of claim 1, wherein the second height is measured from a first location on the first arm top surface to a second location on the first arm bottom surface, and the first arm top surface is parallel to the first arm bottom surface.

13. A plate configured to be coupled to a spacer to form an intervertebral implant that is configured to be inserted in an intervertebral disc space that is defined by a first vertebral body and a second vertebral body, the plate comprising:
a body portion including a first surface and a second surface offset from the first surface in a first direction, the body portion defining a first hole having a first entry opening with an enclosed shape defined by the first surface and a first exit opening, at least a portion of the first exit opening offset from the first entry opening with respect to a second direction that is oblique to the first direction such that the first hole is configured to receive a bone fixation element that secures the plate to the first vertebral body, the body portion defining a second hole having a second entry opening with an enclosed shape defined by the first surface and a second exit opening, at least a portion of the second exit opening offset from the second entry opening with respect to a third direction that is oblique to the first direction such that the second hole is configured to receive a bone fixation element that secures the plate to the second vertebral body, the body portion further including a top surface and a bottom surface offset from the top surface in a fourth direction that is perpendicular to the first direction, the top surface configured to face the first vertebral body when the plate is inserted in the intervertebral disc space, the bottom surface configured to face the second vertebral body when the plate is inserted in the intervertebral disc space, wherein a portion of the first entry opening is closer to the top surface than an entirety of the second entry opening is to the top surface;
a first arm attached to the body portion such that the first arm extends from the second surface in the first direction and terminates at a first end, the first arm including a first portion and a second portion offset from each other along the first direction, the first portion including a first top arm surface and a first bottom arm surface offset from the first top arm surface in the fourth direction, the second portion including a second top arm surface and a second bottom arm surface offset from the second top arm surface in the fourth direction, the first arm configured such that when the plate is inserted in the intervertebral disc space the first top arm surface and the second top arm surface each face the first vertebral body and the first bottom arm surface and the second bottom arm surface each face the second vertebral body; and
a second arm that extends from the body portion and terminates at a second end, such that respective end surfaces of the first and second ends are separated from each other by a distance measured in a fifth direction that is perpendicular to both the first direction and the fourth direction, wherein the first end and the second end comprise respective linear arrays of teeth that face each other and are disposed between the top surface and the bottom surface of the body portion,
wherein the first portion defines a first height measured from the first top arm surface to the first bottom arm surface in the fourth direction, the second portion defines a second height measured from the second top arm surface to the second bottom arm surface in the fourth direction, and the first height is greater than the second height, and
wherein at least a portion of the first entry opening is aligned with at least a portion of the second entry opening with respect to the fifth direction.

14. The plate of claim 13, wherein both the first portion and the second portion are offset from the exit opening in the first direction.

15. The plate of claim 13, wherein the body portion defines a third height measured from the top surface to the bottom surface in the fourth direction, and the third height is greater than the second height.

16. The plate of claim 13, wherein the second arm is offset from the first arm by a gap that is configured to receive the spacer.

17. The plate of claim 13, wherein the second arm includes a third portion and a fourth portion offset from each other along the first direction, the third portion including a third top arm surface and a fourth bottom surface offset from the third top arm surface in the fourth direction, the fourth portion including a fourth top arm surface and a fourth bottom surface offset from the fourth top arm surface in the fourth direction, the second arm configured such that when the plate is inserted in the intervertebral disc space the third top arm surface and the fourth top arm surface each face the first vertebral body and the third bottom surface and the fourth bottom surface each face the second vertebral body.

18. The plate of claim 17, wherein the third portion defines a third height measured from the third top arm surface to the third bottom surface in the fourth direction, the fourth portion defines a fourth height measured from the fourth top arm surface to the fourth bottom surface in the fourth direction, and the third height is greater than the fourth height.

19. The plate of claim 18, wherein the body portion defines a fifth height measured from the top surface to the bottom surface in the fourth direction, the fifth height is greater than the second height, and the fifth height is greater than the fourth height.

20. The plate of claim 18, wherein each of the first portion, the second portion, the third portion, and the fourth portion are offset from the exit opening in the first direction.

21. The plate of claim 18, wherein the first arm includes a first sidewall and a second sidewall that is opposite the first sidewall, the second arm includes a first sidewall that faces the first sidewall of the first arm, the second arm further includes a second sidewall opposite the first sidewall of the second arm, and the second sidewall of the first arm converges toward the second sidewall of the second arm as the first arm extends in the first direction.

\* \* \* \* \*